(12) United States Patent
Inubushi et al.

(10) Patent No.: US 9,586,170 B2
(45) Date of Patent: Mar. 7, 2017

(54) METAL COMPLEX, AND ADSORBENT MATERIAL, STORAGE MATERIAL AND SEPARATION MATERIAL COMPRISING METAL COMPLEX

(71) Applicant: KURARAY CO., LTD., Kurashiki-shi (JP)

(72) Inventors: Yasutaka Inubushi, Kurashiki (JP); Chikako Ikeda, Kurashiki (JP); Takashi Hori, Kurashiki (JP); Masanori Miura, Kurashiki (JP); Takuya Inagaki, Kurashiki (JP)

(73) Assignee: KURARAY CO., LTD., Kurashiki-shi (JP)

( * ) Notice: Subject to any disclaimer, the term of this patent is extended or adjusted under 35 U.S.C. 154(b) by 106 days.

(21) Appl. No.: 14/410,681

(22) PCT Filed: Jun. 28, 2013

(86) PCT No.: PCT/JP2013/067908
§ 371 (c)(1),
(2) Date: Dec. 23, 2014

(87) PCT Pub. No.: WO2014/007179
PCT Pub. Date: Jan. 9, 2014

(65) Prior Publication Data
US 2015/0144085 A1 May 28, 2015

(30) Foreign Application Priority Data

Jul. 2, 2012 (JP) ................................. 2012-148649
Dec. 6, 2012 (JP) ................................. 2012-267264

(51) Int. Cl.
*B01D 53/02* (2006.01)
*F17C 11/00* (2006.01)
(Continued)

(52) U.S. Cl.
CPC ......... *B01D 53/0462* (2013.01); *B01D 53/02* (2013.01); *B01D 53/047* (2013.01);
(Continued)

(58) Field of Classification Search
CPC .. B01D 53/02; B01D 53/047; B01D 53/0462; B01D 2253/112; B01D 2253/204;
(Continued)

(56) References Cited

U.S. PATENT DOCUMENTS

2011/0237796 A1* 9/2011 Inubushi ............... C07C 65/105
546/4
2012/0312164 A1 12/2012 Inubushi et al.
2014/0190436 A1 7/2014 Inubushi et al.

FOREIGN PATENT DOCUMENTS

JP 2000-109485 A 4/2000
JP 2003-342260 A 12/2003
(Continued)

OTHER PUBLICATIONS

International Search Report issued Sep. 24, 2013 in PCT/JP2013/067908 filed Jun. 28, 2013.
(Continued)

*Primary Examiner* — Frank Lawrence
(74) *Attorney, Agent, or Firm* — Oblon, McClelland, Maier & Neustadt, L.L.P.

(57) ABSTRACT

The metal complex comprises a multivalent carboxylic acid compound, at least one metal ion selected from ions of metals belonging to Groups 2 to 13 of the periodic table, an organic ligand capable of multidentate binding to the metal ion, and a $C_1$ or $C_2$ monocarboxylic acid compound. The metal complex has excellent gas adsorption, storage, and separation performance as well as excellent durability. The
(Continued)

metal complex is stably present under high temperature and high humidity, and can maintain high adsorption performance.

16 Claims, 15 Drawing Sheets

(51) Int. Cl.

| | |
|---|---|
| B01J 20/22 | (2006.01) |
| B01D 53/04 | (2006.01) |
| C01B 31/20 | (2006.01) |
| C07F 1/08 | (2006.01) |
| C07C 63/28 | (2006.01) |
| B01D 53/047 | (2006.01) |
| B01J 20/28 | (2006.01) |
| F02B 43/02 | (2006.01) |

(52) U.S. Cl.
CPC ........... *B01J 20/223* (2013.01); *B01J 20/226* (2013.01); *B01J 20/28023* (2013.01); *B01J 20/28033* (2013.01); *B01J 20/28038* (2013.01); *C01B 31/20* (2013.01); *C07C 63/28* (2013.01); *C07F 1/08* (2013.01); *F02B 43/02* (2013.01); *F17C 11/005* (2013.01); *B01D 2253/112* (2013.01); *B01D 2253/204* (2013.01); *B01D 2256/10* (2013.01); *B01D 2256/16* (2013.01); *B01D 2256/24* (2013.01); *B01D 2256/245* (2013.01); *B01D 2257/102* (2013.01); *B01D 2257/104* (2013.01); *B01D 2257/108* (2013.01); *B01D 2257/11* (2013.01); *B01D 2257/50* (2013.01); *B01D 2257/504* (2013.01); *B01D 2257/7022* (2013.01); *B01D 2257/7025* (2013.01); *B01D 2259/40011* (2013.01); *Y02C 10/08* (2013.01); *Y02C 20/20* (2013.01); *Y02P 20/152* (2015.11); *Y02P 20/156* (2015.11); *Y02P 20/51* (2015.11); *Y02T 10/32* (2013.01)

(58) Field of Classification Search
CPC ............ B01D 2256/10; B01D 2256/16; B01D 2256/24; B01D 2256/245; B01D 2257/102; B01D 2257/104; B01D 2257/108; B01D 2257/11; B01D 2257/50; B01D 2257/504; B01D 2257/7022; B01D 2257/7025; B01D 2259/40011; B01J 20/223; B01J 20/226; B01J 20/28023; B01J 20/28033; B01J 20/28038; C01B 31/20; C07C 63/28; C07F 1/08; F02B 43/02; F17C 11/005; Y02C 10/08; Y02C 20/20; Y02P 20/152; Y02P 20/156; Y02P 20/51
USPC ............ 95/90, 96; 96/108; 206/0.7; 502/401
See application file for complete search history.

(56) References Cited

FOREIGN PATENT DOCUMENTS

| JP | 2008-208110 A | 9/2008 |
|---|---|---|
| JP | 2010-265245 A | 11/2010 |
| JP | 2011-190256 A | 9/2011 |
| WO | 2011-105521 A1 | 9/2011 |
| WO | 2013/069721 A1 | 5/2013 |

OTHER PUBLICATIONS

U.S. Appl. No. 14/411,598, filed Dec. 29, 2014, Inubushi, et al.
Extended European Search Report issued Jul. 22, 2015 in Patent Application No. 13812482.1.
U.S. Appl. No. 14/762,733, filed Jul. 22, 2015, Inubushi, et al.

\* cited by examiner

METAL COMPLEX, AND ADSORBENT MATERIAL, STORAGE MATERIAL AND SEPARATION MATERIAL COMPRISING METAL COMPLEX

TECHNICAL FIELD

The present invention relates to a metal complex and to an adsorbent material, a storage material, and a separation material comprising the metal complex. More specifically, the present invention relates to a metal complex comprising a multivalent carboxylic acid compound, at least one metal ion, an organic ligand capable of multidentate binding to the metal ion, and a $C_1$ or $C_2$ monocarboxylic acid compound. The metal complex of the present invention is suitable for an adsorbent material, a storage material, or a separation material for adsorbing, storing, or separating gases such as carbon dioxide, hydrogen, carbon monoxide, oxygen, nitrogen, hydrocarbons having from 1 to 4 carbon atoms, noble gases, hydrogen sulfide, ammonia, water vapor, organic vapor, or the like.

BACKGROUND ART

In the fields of deodorization, exhaust gas treatment, and the like, various adsorbent materials have so far been developed. Activated carbon is a representative example of these, and it has been used widely in various industries for the purpose of air cleaning, desulfurization, denitrification, or removal of harmful substances by making use of its excellent adsorption performance. In recent years, demand for nitrogen has been increasing, for example, in semiconductor manufacturing processes and the like. Such nitrogen is produced from air by using molecular sieving carbon according to the pressure swing adsorption process or temperature swing adsorption process. Molecular sieving carbon is also used for separation and purification of various gases such as purification of hydrogen from cracked methanol gas.

When a mixture of gases is separated according to the pressure swing adsorption process or temperature swing adsorption process, it is common practice to separate it based on the difference between the gases in equilibrium adsorption amount or rate of adsorption to molecular sieving carbon or zeolite used as a separation adsorbent material. When the mixture of gases is separated based on the difference in equilibrium adsorption amount, conventional adsorbent materials cannot selectively adsorb only the gas to be removed, and the separation coefficient decreases, making it inevitable that the size of the apparatus used increases. When the mixture of gases is separated into individual gases based on the difference in rate of adsorption, on the other hand, only the gas to be removed can be adsorbed, although it depends on the kind of gas. It is necessary, however, to alternately perform adsorption and desorption, and also in this case, the apparatus used should be larger.

On the other hand, a polymer metal complex has also been developed as an adsorbent material providing superior adsorption performance. The polymer metal complex has features including (1) large surface area and high porosity, (2) high designability, and (3) a change in dynamic structure when exposed to external stimulation. The polymer metal complex is expected to attain adsorption properties that known adsorbent materials do not have.

Patent Literature 1, for example, discloses a process for producing a metal complex comprising a central metal, an organic ligand having a carboxylate group, and a bridging ligand capable of bidentate binding to the central metal, the process comprising the step of adding an organic acid such as formic acid as a catalyst. However, in the process of Patent Literature 1, an organic acid is used as a catalyst, and a metal complex comprising an organic acid as a constituent element is not disclosed.

CITATION LIST

Patent Literature

PTL 1: JP2008-208110A

SUMMARY OF INVENTION

Technical Problem

In the practical application of gas adsorption materials, separation materials, etc., that use a polymer metal complex, improvement in durability of the metal complex itself has been desired in addition to further improvements in adsorption performance, storage performance, and separation performance. For example, water contained in actual gas is known to adversely affect the metal complex, thereby reducing gas adsorption performance. Accordingly, improvement in durability, in particular, in water resistance of the metal complex has been urgently desired.

An object of the present invention is to provide a metal complex that can be used as a gas adsorption material, a gas storage material, or a gas separation material having higher durability, in particular, higher water resistance than conventional materials.

Solution to Problem

As a result of intensive study, the present inventors found that the above object can be achieved by using a metal complex comprising a multivalent carboxylic acid compound, at least one metal ion, an organic ligand capable of multidentate binding to the metal ion, and a $C_1$ or $C_2$ monocarboxylic acid compound. The present invention was thus accomplished.

Specifically, the present invention provides the following.
(1) A metal complex comprising:
  a multivalent carboxylic acid compound,
  at least one metal ion selected from ions of metals belonging to Groups 2 to 13 of the periodic table,
  an organic ligand capable of multidentate binding to the metal ion, and
  a $C_1$ or $C_2$ monocarboxylic acid compound,
  the composition ratio of the multivalent carboxylic acid compound to the monocarboxylic acid compound being in a range such that multivalent carboxylic acid compound: monocarboxylic acid compound=10:1 to 5,000:1.
(2) The metal complex according to (1), wherein the multivalent carboxylic acid compound is a dicarboxylic acid compound.
(3) The metal complex according to (1) or (2), wherein the organic ligand capable of multidentate binding is an organic ligand capable of bidentate binding.
(4) The metal complex according to (3), wherein the organic ligand capable of bidentate binding has a longitudinal length of 7.0 Å or more and 16.0 Å or less.
(5) The metal complex according to any one of (1) to (4), wherein the metal complex is molded into any shape selected from pellets, films, sheets, plates, pipes, tubes, rods, granules, special molded products, fibers, hollow filaments, woven fabrics, knitted fabrics, and non-woven fabrics.

(6) An adsorbent material comprising the metal complex according to any one of (1) to (5).

(7) The adsorbent material according to (6), wherein the adsorbent material is for adsorbing carbon dioxide, hydrogen, carbon monoxide, oxygen, nitrogen, hydrocarbons having from 1 to 4 carbon atoms, noble gases, hydrogen sulfide, ammonia, sulfur oxides, nitrogen oxides, siloxanes, water vapor, or organic vapor.

(8) A storage material comprising the metal complex according to any one of (1) to (5).

(9) The storage material according to (8), wherein the storage material is for storing carbon dioxide, hydrogen, carbon monoxide, oxygen, nitrogen, hydrocarbons having from 1 to 4 carbon atoms, noble gases, hydrogen sulfide, ammonia, water vapor, or organic vapor.

(10) A gas storage device comprising a pressure-resistant container that can be hermetically sealed and that has an inlet and outlet for gas, the pressure-resistant container having a gas storage space inside, and the storage material according to (8) being placed in the gas storage space.

(11) A gaseous-fuel vehicle comprising an internal combustion engine that obtains driving force from fuel gas supplied from the gas storage device according to (10).

(12) A separation material comprising the metal complex according to any one of (1) to (6).

(13) The separation material according to (12), wherein the separation material is for separating carbon dioxide, hydrogen, carbon monoxide, oxygen, nitrogen, hydrocarbons having from 1 to 4 carbon atoms, noble gases, hydrogen sulfide, ammonia, sulfur oxides, nitrogen oxides, siloxanes, water vapor, or organic vapor.

(14) The separation material according to (12), wherein the separation material is for separating methane and carbon dioxide, hydrogen and carbon dioxide, nitrogen and carbon dioxide, ethylene and carbon dioxide, methane and ethane, ethane and ethylene, propane and propene, nitrogen and oxygen, oxygen and argon, nitrogen and methane, or air and methane.

(15) A separation method using the separation material according to (12), the separation method comprising the step of bringing a metal complex into contact with a gas mixture in a pressure range of 0.01 to 10 MPa.

(16) The separation method according to (15), wherein the separation method is a pressure swing adsorption process or a temperature swing adsorption process.

Advantageous Effects of Invention

The present invention provides a metal complex comprising a multivalent carboxylic acid compound, at least one metal ion, an organic ligand capable of multidentate binding to the metal ion, and a $C_1$ or $C_2$ monocarboxylic acid compound. The metal complex of the present invention has excellent durability, in particular, excellent water resistance, and is stably present under high temperature and high humidity. The metal complex of the present invention also has high adsorption performance.

Due to its superior adsorption performance with respect to various gases, the metal complex of the present invention can be used as an adsorbent material for adsorbing carbon dioxide, hydrogen, carbon monoxide, oxygen, nitrogen, hydrocarbons having from 1 to 4 carbon atoms, noble gases, hydrogen sulfide, ammonia, sulfur oxides, nitrogen oxides, siloxanes, water vapor, organic vapor, and the like.

Further, due to its superior storage performance with respect to various gases, the metal complex of the present invention can also be used as a storage material for storing carbon dioxide, hydrogen, carbon monoxide, oxygen, nitrogen, hydrocarbons having from 1 to 4 carbon atoms, noble gases, hydrogen sulfide, ammonia, water vapor, organic vapor, and the like.

Furthermore, due to its superior separation performance with respect to various gases, the metal complex of the present invention can further be used as a separation material for separating gases such as carbon dioxide, hydrogen, carbon monoxide, oxygen, nitrogen, hydrocarbons having from 1 to 4 carbon atoms, noble gases, hydrogen sulfide, ammonia, sulfur oxides, nitrogen oxides, siloxanes, water vapor, organic vapor, and the like.

In the measurement results of a powder X-ray diffraction pattern, the horizontal axis represents a diffraction angle (2θ) and the vertical axis represents a diffraction intensity expressed in cps (counts per second) (FIGS. 4, 8, 11, 13, and 14).

In the measurement results of adsorption and desorption isotherms, the horizontal axis represents an equilibrium pressure expressed in MPa, and the vertical axis represents an equilibrium adsorption amount expressed in mL(STP)/g (FIGS. 17 to 27 and 29). In the measurement results of adsorption and desorption isotherms, the adsorption amounts (ads.) of the gases under increased pressure and the desorption amounts (des.) of the gases under decreased pressure are plotted for each pressure level. "STP" (standard temperature and pressure) denotes a state at a temperature of 273.15 K and a pressure of 1 bar ($10^5$ Pa).

Figure 28:
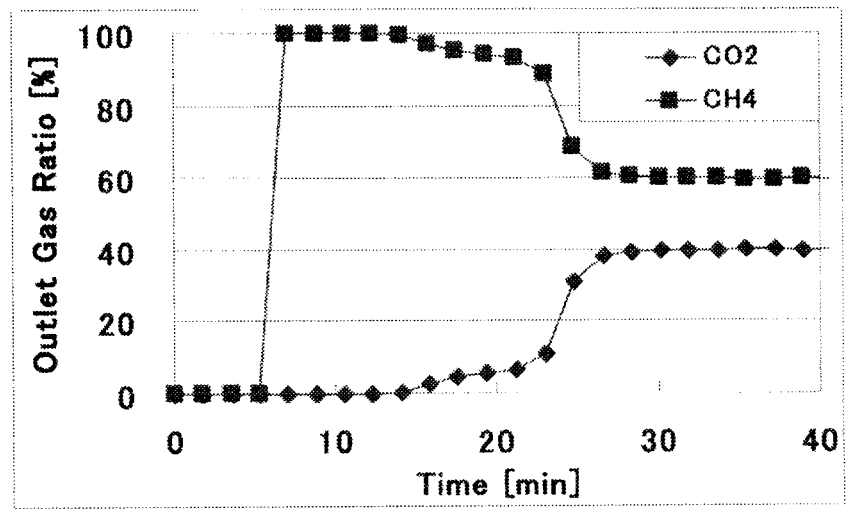
FIG. 28 shows a result for measuring a breakthrough curve at 293 K, 0.8 MPa, and space velocity of 6 $min^{-1}$ on a metal complex obtained in Synthesis Example 2 using a gas mixture comprising methane and carbon dioxide in a volume ratio of methane to carbon dioxide of 60 to 40.

In the measurement result of a breakthrough curve, the horizontal axis represents flow time of gas in minutes (Time [min]) and the vertical axis represents a ratio of an outlet gas (Outlet Gas Ratio [%]) (FIG. 28).

DESCRIPTION OF EMBODIMENTS

The metal complex of the present invention comprises a multivalent carboxylic acid compound, at least one metal ion selected from ions of metals belonging to Groups 2 to 13 of the periodic table, an organic ligand capable of multidentate binding to the metal ion, and a $C_1$ or $C_2$ monocarboxylic acid compound.

The multivalent carboxylic acid compound used in the present invention is not particularly limited. Dicarboxylic acid compounds, tricarboxylic acid compounds, tetracarboxylic acid compounds, etc., can be used. Examples of dicarboxylic acid compounds include succinic acid, 1,4-cyclohexanedicarboxylic acid, fumaric acid, muconic acid, 2,3-pyrazinedicarboxylic acid, isophthalic acid, terephthalic acid, 1,4-naphthalenedicarboxylic acid, 2,6-naphthalenedicarboxylic acid, 2,7-naphthalenedicarboxylic acid, 4,4'-biphenyldicarboxylic acid, 2,5-pyridinedicarboxylic acid, 3,5-pyridinedicarboxylic acid, 2,5-thiophenedicarboxylic acid, 2,2'-dithiophenedicarboxylic acid, and the like. Examples of tricarboxylic acid compounds include trimesic acid, trimellitic acid, biphenyl-3,4',5-tricarboxylic acid, 1,3,5-tris(4-carboxyphenyl)benzene, 1,3,5-tris(4'-carboxy[1,1'-biphenyl]-4-yl)benzene, and the like. Examples of tetracarboxylic acid compounds include pyromellitic acid, [1,1':4',1"]terphenyl-3,3",5,5"-tetracarboxylic acid, 1,2,4,5-tetrakis(4-carboxyphenyl)benzene, and the like. Of these, dicarboxylic acid compounds are preferable; more preferable are unsaturated dicarboxylic acid compounds (e.g., fumaric acid, 2,3-pyrazinedicarboxylic acid, isophthalic acid, terephthalic acid, 1,4-naphthalenedicarboxylic acid, 2,6-naphthalenedicarboxylic acid, 2,7-naphthalenedicarboxylic acid, 9,10-anthracenedicarboxylic acid, 4,4'-biphenyldicarboxylic acid, 4,4'-stilbenedicarboxylic acid, 2,5-pyridinedicarboxylic acid, 3,5-pyridinedicarboxylic acid, 2,5-thiophenedicarboxylic acid, and 2,2'-dithiophenedicarboxylic acid). The multivalent carboxylic acid compounds can be used singly or in a mixture of two or more. The metal complex of the present invention may be a mixture of two or more metal complexes each containing a single multivalent carboxylic acid compound.

The multivalent carboxylic acid compound may be used in the form of acid anhydride or alkali metal salt.

The multivalent carboxylic acid compound may further comprise a substituent other than carboxyl. The multivalent carboxylic acid having a substituent is preferably an aromatic multivalent carboxylic acid, and a substituent preferably binds to the aromatic ring of the aromatic multivalent carboxylic acid. The number of substituents is 1, 2, or 3. Examples of substituents include, but are not particularly limited to, alkyl groups (linear or branched alkyl groups having from 1 to 5 carbon atoms, such as methyl, ethyl, n-propyl, isopropyl, n-butyl, isobutyl, tert-butyl, and pentyl), halogen atoms (fluorine, chlorine, bromine, and iodine), alkoxy groups (e.g., methoxy, ethoxy, n-propoxy, isopropoxy, n-butoxy, isobutoxy, and tert-butoxy), amino groups, monoalkylamino groups (e.g., methylamino), dialkylamino groups (e.g., dimethylamino), formyl groups, epoxy groups, acyloxy groups (e.g., acetoxy, n-propanoyloxy, n-butanoyloxy, pivaloyloxy, and benzoyloxy), alkoxycarbonyl groups (e.g., methoxycarbonyl, ethoxycarbonyl, and n-butoxycarbonyl), nitro groups, cyano groups, hydroxyl groups, acetyl groups, trifluoromethyl groups, and the like. Specific examples include multivalent carboxylic acid compounds having a substituent such as 2-nitroterephthalic acid, 2-fluoroterephthalic acid, 1,2,3,4-tetrafluoro terephthalic acid, 2,4,6-trifluoro-1,3,5-benzenetricarboxylic acid, and the like.

In the present invention, at least one metal ion selected from ions of metals belonging to Groups 2 to 13 of the periodic table is used. The ions of metals belonging to Group 2 of the periodic table include beryllium, magnesium, calcium, strontium, barium, and radium ions. The ions of metals belonging to Group 3 of the periodic table include scandium, yttrium, lanthanide, and actinoid ions. The ions of metals belonging to Group 4 of the periodic table include titanium, zirconium, hafnium, and rutherfordium ions. The ions of metals belonging to Group 5 of the periodic table include vanadium, niobium, tantalum, and dubnium ions.

The ions of metals belonging to Group 6 of the periodic table include chromium, molybdenum, tungsten, and seaborgium ions. The ions of metals belonging to Group 7 of the periodic table include manganese, technetium, rhenium, and bohrium ions. The ions of metals belonging to Group 8 of the periodic table include iron, ruthenium, osmium, and hassium ions. The ions of metals belonging to Group 9 of the periodic table include cobalt, rhodium, iridium, and meitnerium ions. The ions of metals belonging to Group 10 of the periodic table include nickel, palladium, platinum, and darmstadtium ions. The ions of metals belonging to Group 11 of the periodic table include copper, silver, gold, and roentgenium ions. The ions of metals belonging to Group 12 of the periodic table include zinc, cadmium, mercury, and copernicium ions. The ions of metals belonging to Group 13 of the periodic table include boron, aluminum, gallium, indium, thallium, and ununtrium ions.

Examples of ions of metals belonging to Groups 2 to 13 of the periodic table preferably used in the present invention include magnesium, calcium, scandium, lanthanide (e.g., lantern, terbium, and lutetium), actinoid (e.g., actinium and lawrencium), zirconium, vanadium, chromium, molybdenum, manganese, iron, cobalt, nickel, copper, zinc, cadmium, aluminum, and like ions. Of these, manganese, cobalt, nickel, copper, and zinc ions are preferable, and copper ions are particularly preferable. It is preferable to use a single metal ion; however, it is also possible to use two or more metal ions. The metal complex of the present invention may be a mixture of two or more metal complexes each containing a single metal ion.

The metal ion can be used in the form of metal salt. Usable examples of metal salts include magnesium salts, calcium salts, scandium salts, lanthanide salts (e.g., lantern salt, terbium salt, and lutetium salt), actinoid salts (e.g., actinium salt, and lawrencium salt), zirconium salts, vanadium salts, chromium salts, molybdenum salts, manganese salts, iron salts, cobalt salts, nickel salts, copper salts, zinc salts, cadmium salts, and aluminum salts. Of these, manganese salts, cobalt salts, nickel salts, copper salts, and zinc salts are preferable, and copper salts are more preferable. It is preferable to use a single metal salt; however, it is also possible to use a mixture of two or more metal salts. Examples of such metal salts include organic acid salts such as acetates and formates, and inorganic acid salts such as sulfates, nitrates, hydrochlorides, hydrobromates, and carbonates.

The organic ligand capable of multidentate binding used in the present invention refers to a neutral ligand having at least two sites coordinated to a metal ion with a lone electron pair.

Examples of sites coordinated to a metal ion with a lone electron pair include a nitrogen atom, an oxygen atom, a phosphorus atom, a sulfur atom, and the like. The organic ligand capable of multidentate binding is preferably a heterocyclic compound, in particular, a heterocyclic compound that has a nitrogen atom as coordination sites. The heterocyclic compound may have a substituent, or may be bound to a divalent hydrocarbon group (for example, a divalent group in which two hydrogen atoms are removed from ethyne).

The organic ligand capable of multidentate binding to the meal ion used in the present invention is not particularly limited; however, organic ligands capable of bidentate binding to the metal ion, organic ligands capable of tridentate binding to the metal ion, organic ligands capable of tetradentate binding to the metal ion, etc., can be used. Examples of organic ligands capable of bidentate binding (bidentate organic ligands) include 1,4-diazabicyclo[2.2.2]octane, pyrazine, 2,5-dimethylpyrazine, 4,4'-bipyridyl, 2,2'-dimethyl-4,4'-bipyridine, 2,7-diazapyrene, 1,2-bis(4-pyridyl)ethyne, 1,4-bis(4-pyridyl)butadiyne, 1,4-bis(4-pyridyl)benzene, 3,6-di(4-pyridyl)-1,2,4,5-tetrazine, 2,2'-bi-1,6-naphthyridine, phenazine, diazapyrene, trans-1,2-bis(4-pyridyl)ethene, 4,4'-azopyridine, 1,2-bis(4-pyridyl)ethane, 4,4'-dipyridyl sulfide, 1,3-bis(4-pyridyl)propane, 1,2-bis(4-pyridyl)-glycol, N-(4-pyridyl)isonicotinamide, 1,2-bis(1-imidazolyl)ethane, 1,2-bis(1,2,4-triazolyl)ethane, 1,2-bis(1,2,3,4-tetrazolyl)ethane, 1,3-bis(1-imidazolyl)propane, 1,3-bis(1,2,4-trizolyl)propane, 1,3-bis(1,2,3,4-tetrazolyl)propane, 1,4-bis(4-pyridyl)butane, 1,4-bis(1-imidazolyl)butane, 1,4-bis(1,2,4-triazolyl)butane, 1,4-bis(1,2,3,4-tetrazolyl)butane, 1,4-bis(benzimidazole-1-ylmethyl)-2,4,5,6-tetramethyl benzene, 1,4-bis(4-pyridylmethyl)-2,3,5,6-tetramethyl benzene, 1,3-bis(imidazole-1-ylmethyl)-2,4,6-trimethyl benzene, 1,3-bis(4-pyridylmethyl)-2,4,6-trimethyl benzene, 2,6-di(4-pyridyl)-benzo[1,2-c:4,5-c']dipyrrole-1,3,5,7(2H,6H)-tetrone, 4,4'-bis(4-pyridyl)biphenylene, N,N'-di(4-pyridyl)-1,4,5,8-naphthalene tetracarboxy diimide, and the like. Examples of organic ligands capable of tridentate binding (tridentate organic ligands) include 1,3,5-tris(2-pyridyl)benzene, 1,3,5-tris(3-pyridyl)benzene, 1,3,5-tris(4-pyridyl)benzene, 1,3,5-tris(1-imidazolyl)benzene, 2,4,6-tris(2-pyridyl)-1,3,5-triazine, 2,4,6-tris(3-pyridyl)-1,3,5-triazine, 2,4,6-tris(4-pyridyl)-1,3,5-triazine, 2,4,6-tris(1-imidazolyl)-1,3,5-triazine, and the like. Examples of organic ligands capable of tetradentate binding (tetradentate organic ligands) include 1,2,4,5-tetrakis(2-pyridyl)benzene, 1,2,4,5-tetrakis(3-pyridyl)benzene, 1,2,4,5-tetrakis(4-pyridyl)benzene, 1,2,4,5-tetrakis(1-imidazolyl)benzene, tetrakis(4-pyridyloxymethylene)methane, tetrakis(1-imidazolylmethyl)methane, and the like. Of these, organic ligands capable of bidentate binding are preferable. The organic ligands capable of multidentate binding can be used singly or in a mixture of two or more. The metal complex of the present invention may be a mixture of two or more metal complexes each containing a single organic ligand capable of multidentate binding.

Of the organic ligands capable of multidentate binding, an organic ligand capable of bidentate binding that belongs to the $D_{\infty h}$ point group and has a longitudinal length of 7.0 Å or more and 16.0 Å or less is preferable. The point group to which the organic ligand capable of bidentate binding belongs may be determined according to the method disclosed in Reference Document 1 below.

Reference Document 1: *Bunshino Taisho to Gunron*, Molecular Symmetry and Group Theory; Masao Nakazaki, 1973, Tokyo Kagaku Dojin Co., Ltd., pp. 39-40.

For example, since 4,4'-bipyridyl, 1,2-bis(4-pyridyl)ethyne, 2,7-diazapyrene, 1,4-bis(4-pyridyl)benzene, 3,6-di(4-pyridyl)-1,2,4,5-tetrazine, 2,6-di(4-pyridyl)-benzo[1,2-c:4,5-c']dipyrrole-1,3,5,7(2H,6H)-tetorone, 4,4'-bis(4-pyridyl)biphenylene, N,N'-di(4-pyridyl)-1,4,5,8-naphthalene tetracarboxy diimide, and the like are bilaterally symmetric linear molecules having a symmetric center, they belong to the $D_{\infty h}$ point group. Further, since 1,2-bis(4-pyridyl)ethene has a two-fold axis and symmetric planes perpendicular to the axis, it belongs to the $C_{2h}$ point group.

When the point group of the organic ligand capable of bidentate binding is $D_{\infty h}$, the high symmetry reduces wasteful gaps. Thus, high adsorption performance can be exhibited. In addition, when the longitudinal length of the organic ligand capable of bidentate binding is 7.0 Å or more and 16.0 Å or less, the distance between the metal ions in the metal complex will be suitable. Thus, a metal complex having optimal gaps for adsorbing and desorbing a gas molecule can be formed.

The longitudinal length of the organic ligand capable of bidentate binding in the present specification is defined as the distance between two atoms having the longest distance between them, among the atoms coordinated to the metal ion in the structural formula, in the most stable structure found by structure optimization according to the PM5 semiempirical molecular orbital method after the conformational analysis according to the MM3 molecular dynamics method using Scigress Explorer Professional Version 7.6.0.52 (produced by Fujitsu).

For example, the interatomic distance between nitrogen atoms of pyrazine is 2.810 Å, the interatomic distance between nitrogen atoms of 4,4'-bipyridyl is 7.061 Å, the interatomic distance between nitrogen atoms of 1,2-bis(4-pyridyl)ethyne is 9.583 Å, the interatomic distance between nitrogen atoms of 1,4-bis(4-pyridyl)benzene is 11.315 Å, the interatomic distance between nitrogen atoms of 3,6-di(4-pyridyl)-1,2,4,5-tetrazine is 11.204 Å, the interatomic distance between nitrogen atoms of 2,6-di(4-pyridyl)-benzo[1,2-c:4,5-c']dipyrrole-1,3,5,7(2H,6H)-tetrone is 15.309 Å, the interatomic distance between nitrogen atoms of 4,4'-bis(4-pyridyl)biphenyl is 15.570 Å, and the interatomic distance between nitrogen atoms of N,N'-di(4-pyridyl)-1,4,5,8-naphthalene tetracarboxy diimide is 15.533 Å. Of the organic ligands capable of bidentate binding that belong to the $D_{\infty h}$ point group, and have a longitudinal length of 7.0 Å or more and 16.0 Å or less, 4,4'-bipyridyl is particularly preferably used.

Examples of $C_1$ or $C_2$ monocarboxylic acid compounds used in the present invention include formic acid, acetic acid, trifluoroacetic acid, etc. Of these, formic acid or acetic acid is preferable, and acetic acid is particularly preferable. The monocarboxylic acid compounds can be used singly or in a mixture of two or more. The metal complex of the present invention may be a mixture of two or more metal complexes each containing a single monocarboxylic acid compound.

The monocarboxylic acid compound may be used in the form of acid anhydride or alkali metal salt in the manufacture of the metal complex. The monocarboxylic acid compound can be incorporated in the metal complex structure of the present invention when used as a counteranion of the raw material metal salt. For example, when a copper ion and acetic acid are respectively used as a metal ion and a monocarboxylic acid compound, copper acetate can be used as the raw material metal salt. The monocarboxylic acid compound may be present from the early stage of the reaction, or may be added in the latter stage of the reaction (for example, after reacting components other than the monocarboxylic acid compound).

The composition ratio of the multivalent carboxylic acid compound to the $C_1$ or $C_2$ monocarboxylic acid compound composing the metal complex of the present invention is preferably such that multivalent carboxylic acid compound:$C_1$ or $C_2$ monocarboxylic acid compound=10:1 to 5,000:1, more preferably 10:1 to 2,500:1, and even more preferably 20:1 to 1,000:1.

The composition ratio of the organic ligand capable of multidentate binding to the $C_1$ or $C_2$ monocarboxylic acid compound composing the metal complex of the present invention is preferably such that organic ligand capable of multidentate binding:$C_1$ or $C_2$ monocarboxylic acid compound=10:1 to 5,000:1, more preferably 50:1 to 1,250:1, and even more preferably 100:1 to 500:1.

The composition ratio of the multivalent carboxylic acid compound to the $C_1$ or $C_2$ monocarboxylic acid compound composing the metal complex of the present invention can be determined by analysis using, for example, gas chromatography, high-performance liquid chromatography, or NMR after the metal complex is dissolved to obtain a homogeneous solution. However, the method is not limited to them.

The metal complex of the present invention may further include a monodentate organic ligand as long as the effect of the present invention is not impaired. The monodentate organic ligand refers to a neutral ligand having one site coordinated to a metal ion with a lone electron pair. Examples of monodentate organic ligands include substituted or unsubstituted furan, thiophene, pyridine, quinoline, isoquinoline, acridine, trimethyl phosphine, triphenyl phosphine, triphenyl phosphite, methylisocyanide, and the like. Of these, pyridine is preferable. The monodentate organic ligand may include a $C_{1-23}$ hydrocarbon group as a substituent.

When the metal complex of the present invention includes the monodentate organic ligand, the proportion of the monodentate organic ligand is not particularly limited as long as the effect of the present invention is not impaired. For example, the composition ratio of the organic ligand capable of multidentate binding to the monodentate organic ligand is preferably such that organic ligand capable of multidentate binding:monodentate organic ligand=1:10 to 5,000:1, more preferably 1:20 to 5,000:1, even more preferably 20:1 to 5,000:1, and particularly preferably 100:1 to 2,500:1. The composition ratio can be determined by analysis using, for example, gas chromatography, high-performance liquid chromatography, or NMR; however, the method is not limited to them.

The metal complex of the present invention can be produced by reacting a multivalent carboxylic acid compound, at least one metal salt selected from salts of metals belonging to Groups 2 to 13 of the periodic table, an organic ligand capable of multidentate binding to the metal ion, a $C_1$ or $C_2$ monocarboxylic acid compound, and optionally a monodentate organic ligand in vapor phase, liquid phase, or solid phase. The metal complex of the present invention is preferably produced by reacting these components in a solvent under ordinary pressure for several hours to several days, and precipitating them. The reaction may be performed under ultrasonic or microwave irradiation. For example, the metal complex of the present invention can be obtained by mixing and reacting a metal salt aqueous solution or an organic solvent solution with an aqueous solution or an organic solvent solution containing a multivalent carboxylic acid compound, an organic ligand capable of multidentate binding, and a monocarboxylic acid compound, under ordinary pressure.

The mixing ratio of the metal salt to the multivalent carboxylic acid compound during the manufacture of the metal complex is preferably in the following molar ratio: metal salt:multivalent carboxylic acid compound=1:5 to 8:1, and more preferably 1:3 to 6:1.

The mixing ratio of the metal salt to the organic ligand capable of multidentate binding during the manufacture of the metal complex is preferably in the following molar ratio: metal salt:organic ligand capable of multidentate binding=1:3 to 3:1, and more preferably 1:2 to 2:1. If the mixing ratio falls out of this range, the yield of the target metal complex decreases, and residues of unreacted raw materials are generated, thereby causing complication in the purification process of the resulting metal complex.

The mixing ratio of the multivalent carboxylic acid compound to the $C_1$ or $C_2$ monocarboxylic acid compound during the manufacture of the metal complex is preferably in the following molar ratio: multivalent carboxylic acid compound:$C_1$ or $C_2$ monocarboxylic acid compound=1:1,000 to 5,000:1, and more preferably 1:100 to 1,000:1. If the mixing ratio falls out of this range, the yield of the target metal complex decreases, and residues of unreacted raw materials are generated, thereby causing complication in the purification process of the resulting metal complex.

The particle size or morphology of the metal complex of the present invention can be controlled according to the type and amount of the $C_1$ or $C_2$ monocarboxylic acid compound used.

The molar concentration of the multivalent carboxylic acid compound in the mixed solution used for the manufacture of the metal complex is preferably 0.01 to 5.0 mol/L, and more preferably 0.05 to 2.0 mol/L. If the molar concentration falls below this range upon the reaction, the yield of reaction undesirably decreases even though the target metal complex can still be obtained. If the molar concentration falls above this range upon the reaction, the solubility decreases, thereby hindering the smooth progress of reaction.

The molar concentration of the metal salt in the mixed solution used for the manufacture of the metal complex is preferably 0.01 to 5.0 mol/L, and more preferably 0.05 to 2.0 mol/L. If the molar concentration falls below this range upon the reaction, the yield of reaction undesirably decreases even though the target metal complex can still be obtained. If the molar concentration falls above this range, residues of unreacted metal salts are generated, thereby causing complication in the purification process of the resulting metal complex.

The molar concentration of the organic ligand capable of multidentate binding in the mixed solution used for the manufacture of the metal complex is preferably 0.005 to 2.5 mol/L, and more preferably 0.025 to 1.0 mol/L. If the molar concentration falls below this range upon the reaction, the yield of reaction undesirably decreases even though the target metal complex can still be obtained. If the molar concentration falls above this range upon the reaction, the solubility decreases, thereby hindering the smooth progress of reaction.

The solvent used for the manufacture of metal complex may be an organic solvent, water, or a mixed solvent of these. Specific examples of solvents include methanol, ethanol, propanol, diethylether, butanol, dimethoxyethane, tetrahydrofuran, hexane, cyclohexane, heptane, benzene, toluene, methylene chloride, chloroform, acetone, ethyl acetate, acetonitrile, N,N-dimethylformamide, water, and mixed solvents of these substances.

The reaction temperature can be suitably selected according to the solvent used, and it is preferably 253 to 463 K, and more preferably 298 to 423 K.

The completion of the reaction may be confirmed by analyzing the remaining amount of the raw materials by using absorption spectrophotometry, gas chromatography, or high-performance liquid chromatography; however, the method is not limited to them. After the reaction is completed, the resulting mixture is subjected to suction filtration to collect the precipitates. The precipitates are washed with an organic solvent and dried in vacuum for several hours at about 373 K, thereby obtaining the metal complex of the present invention.

Since the metal complex of the present invention is a porous material and can adsorb and desorb a low molecule such as gas in the micropores, it can be used as an adsorbent material, storage material, and separation material for various gases. However, the metal complex does not adsorb gas when a solvent used in manufacture is adsorbed. Accordingly, when the metal complex is used as the adsorbent material, storage material, or separation material of the present invention, it is necessary to dry the metal complex under vacuum in advance to remove the solvent in the micropores. The vacuum drying may be generally performed at a temperature that does not decompose the metal complex (e.g., 298 K to 523 K or less); however, an even lower temperature (e.g., 298 K to 393 K or less) is preferable. This operation may be replaced by washing with supercritical carbon dioxide, which is more efficient.

The metal complex of the present invention has a one-dimensional, two-dimensional, or three-dimensional framework, depending on the type of multivalent carboxylic acid compound, metal ion, and organic ligand capable of multidentate binding to the metal ion to be used.

Examples of frameworks of the metal complex include a three-dimensional structure in which two jungle-gym-type frameworks are interpenetrated into each other; a three-dimensional structure composed of two-dimensional-sheet-type frameworks obtained by using a copper ion as a metal ion, 2,5-dihydroxybenzoate ion as a multivalent carboxylic acid compound, and 4,4'-bipyridyl as an organic ligand capable of multidentate binding; and the like.

The particle size or morphology of the metal complex of the present invention can be controlled according to the type and amount of the monocarboxylic acid compound used.

The particle size of the metal complex can be confirmed by using a laser diffraction method, a dynamic light scattering method, an imaging method, a settling method, or the like; however, the method is not limited to them.

Figure 1:
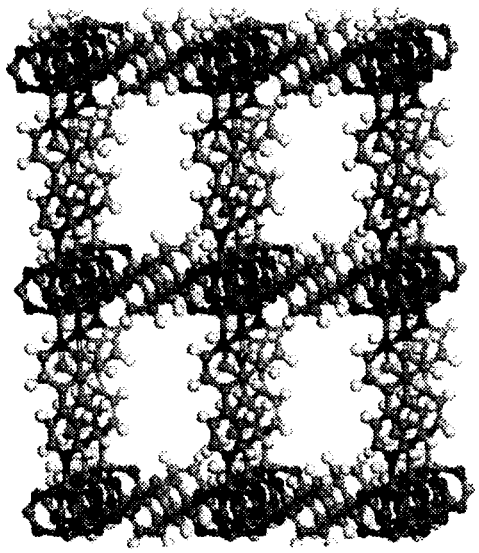
FIG. 1 shows a schematic diagram illustrating a jungle-gym-type framework in which 4,4'-bipyridyl is coordinated to the axial position of a metal ion in a paddle-wheel-type framework composed of a zinc ion and a carboxylate ion of terephthalic acid.
Figure 2:
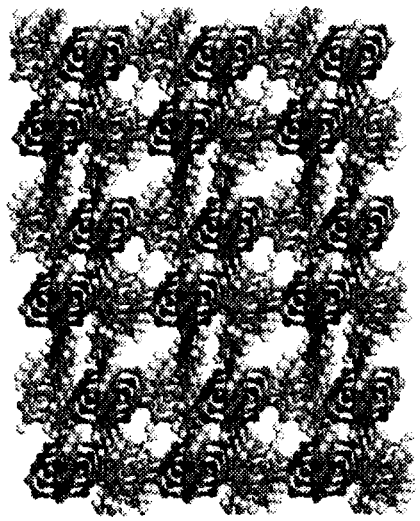
FIG. 2 is a schematic diagram illustrating a three-dimensional structure in which two jungle-gym-type frameworks are interpenetrated into each other.

One detailed example is a metal complex comprising terephthalic acid as a multivalent carboxylic acid compound, zinc ion as a metal ion, and 4,4'-bipyridyl as an organic ligand capable of multidentate binding. The metal complex of the present invention thus obtained has a three-dimensional structure composed of interpenetrated two jungle-gym-type frameworks. The jungle-gym-type framework is structured such that 4,4'-bipyridyl is coordinated to the axial position of a metal ion in a paddle-wheel-type framework composed of a metal ion and a carboxylate ion of terephthalic acid. FIG. 1 is a schematic diagram illustrating a jungle-gym-type framework, and FIG. 2 is a schematic diagram illustrating a three-dimensional structure in which two jungle-gym-type frameworks are interpenetrated into each other.

The "jungle-gym-type framework" is defined as a jungle-gym-like three-dimensional structure in which an organic ligand capable of multidentate binding is coordinated to the axial position of a metal ion in a paddle-wheel-type framework composed of a metal ion and a multivalent carboxylic acid compound such as terephthalic acid, thus connecting the two-dimensional lattice sheets composed of the multivalent carboxylic acid compound and the metal ion. "A structure in which multiple jungle-gym-type frameworks are interpenetrated into each other" is defined as a three-dimensional framework in which multiple jungle-gym-type frameworks are interpenetrated into each other by filling each other's micropores.

For example, single-crystal X-ray structure analysis, powder X-ray crystal structure analysis, and single-crystal neutron structure analysis may be used to confirm whether the metal complex has the structure in which multiple junglegym-type frameworks are interpenetrated into each other; however, the method is not limited to them.

By reacting the multivalent carboxylic acid compound with the metal ion in the presence of the $C_1$ or $C_2$ monocarboxylic acid compound, the reaction of the metal ion and the multivalent carboxylic acid compound, and the reaction of the metal ion and the monocarboxylic acid compound will compete with each other. When coordinated to the metal ion, since the monocarboxylic acid compound has only one coordination site, the crystal growth at the coordination site stops. Accordingly, the monodentate organic ligand can be considered to be a terminator for crystal growth reaction. However, since the reaction of the metal ion and the monocarboxylic acid compound is reversible, the crystal nucleation rate and the crystal growth rate are controlled. Consequently, the particle size or morphology can be adjusted, and the metal complex having less crystal defect can be obtained. Since the crystal defect can be a point at which decomposition of the metal complex is initiated, the metal complex of the present invention, which has fewer crystal defects, has, for example, excellent resistance to water vapor.

The above water resistance improvement mechanism is estimation. Even if water resistance improvement mechanism does not conform to the above mechanism, it will be covered within the technical scope of the present invention insofar as it satisfies the requirements specified in the present invention.

The water resistance of the metal complex in the present invention can be evaluated, for example, by measuring the change in adsorption amount before and after exposure to water vapor.

The metal complex of the present invention has excellent adsorption performance, storage performance, and separation performance with respect to various gases. Accordingly, the metal complex of the present invention is useful as an adsorbent material, a storage material, or a separation material for various gases, which are also within the technical scope of the present invention.

The adsorbent material, the storage material, or the separation material of the present invention can be used preferably for adsorbing, storing, or separating carbon dioxide, hydrogen, carbon monoxide, oxygen, nitrogen, hydrocarbons having from 1 to 4 carbon atoms (such as methane, ethane, ethylene, acetylene, propane, propene, methylacetylene, propadiene, butane, 1-butene, isobutene, 1-butyne, 2-butyne, 1,3-butadiene, and methylallene), noble gases (such as helium, neon, argon, krypton, and xenon), hydrogen sulfide, ammonia, sulfur oxides, nitrogen oxides, siloxanes (such as hexamethylcyclotrisiloxane and octamethylcyclotetrasiloxane), water vapor, and organic vapor. The separation material of the present invention is suitable for separating methane and carbon dioxide, hydrogen and carbon dioxide, nitrogen and carbon dioxide, ethylene and carbon dioxide, methane and ethane, ethylene and ethane, nitrogen and oxygen, oxygen and argon, nitrogen and methan, or air and methane by using a pressure swing adsorption process or a temperature swing adsorption process.

The term "organic vapor" means a vaporizing gas of an organic substance that is in liquid form at ordinary temperature under ordinary pressure. Examples of such organic substances include alcohols, such as methanol and ethanol; amines, such as trimethylamine; aldehydes, such as formaldehyde and acetaldehyde; hydrocarbons having 5 to 16 carbon atoms, such as pentane, isoprene, hexane, cyclohexane, heptane, methylcyclohexane, octane, 1-octene, cyclooctane, cyclooctene, 1,5-cyclooctadiene, 4-vinyl-1-cyclohexene, and 1,5,9-cyclododecatriene; aromatic hydrocarbons, such as benzene and toluene; ketones, such as acetone and methyl ethyl ketone; esters, such as methyl acetate and ethyl acetate; and halogenated hydrocarbons, such as methyl chloride and chloroform.

The metal complex, or the adsorbent material, storage material, and separation material of the present invention can be used in any form. They can be used in the form of powders without any treatment, or can be formed into pellets, films, sheets, plates, pipes, tubes, rods, granules, various special molded products, fibers, hollow filaments, woven fabrics, knitted fabrics, non-woven fabrics, and the like. The metal complex, or the adsorbent material, storage material, and separation material of the present invention, which are molded into the above form, has improved handling properties, and can be used in wide applications.

The metal complex, or the adsorbent material, storage material, and separation material of the present invention can be molded optionally using a binder such as titanium dioxide, silica dioxide, aluminum oxide, montmorillonite, kaolin, bentonite, halloysite, dickite, nacrite, anauxite, tetraalkoxysilane (e.g., tetramethoxysilane, tetraethoxysilane, tetrapropoxysilane, and tetrabutoxysilane), starch, cellulose, cellulose acetate, polyvinyl alcohol, polyamide, polyester, polycarbonate, polysulfone, polyethersulfone, polyolefin, polytetrafluoroethylene, elastomer, etc., within a range that does not impair the effect of the present invention. The concentration of the binder in the molded product is generally 0.1 to 99 mass %, preferably 0.1 to 90 mass %, and more preferably 0.5 to 50 mass %. Additionally, natural or synthetic fibers such as paper, or inorganic fibers such as glass or alumina may also be combined.

Of these, an elastomer is preferably used as a binder in view of molding properties. The elastomer used is not particularly limited, and any elastomer can be used. In particular, thermoplastic elastomers are preferable. Usable thermoplastic elastomers are block copolymers having, as part of the polymer chain, at least one polymer block (rubber phase) with a glass transition temperature of 273 K or less. Particularly preferable thermoplastic elastomers are block copolymers having, as part of the polymer chain, a polymer block (rubber phase) with a glass transition temperature of 273 K or less, and a polymer block (constrained phase) with a glass transition temperature of 310 K or more.

Examples of thermoplastic elastomers include styrene elastomers, olefin elastomers, urethane elastomers, polyester elastomers, nitrile elastomers, amide elastomers, polybutadiene elastomers, acrylic elastomers, and vinyl chloride elastomers. Of these, styrene elastomers, olefin elastomers, and acrylic elastomers are particularly preferably used.

The method for producing pellets comprising the metal complex, or the adsorbent material, storage material, or separation material, of the present invention is not particularly limited, and any known pelletizing method can be used. To produce pellets with a higher density, tablet compression is preferable. In tablet compression, the metal complex, or the composition of the metal complex and a binder, is generally prepared in advance, and then solidified in a specific shape under pressure using a commercially available tablet compression machine. During this process, a lubricant such as black lead and magnesium stearate may be added to the preparation product, as necessary.

The method for producing sheets comprising the metal complex, or the adsorbent material, storage material, or separation material of the present invention is not particularly limited, and any known sheet-forming method can be used. To produce sheets with a higher density, wet paper making is preferable. Wet paper making is a method in which raw materials are dispersed in water and filtered through a net, followed by drying.

An example of special molded products is a honeycomb shape. Any known processing method can be used to form sheets comprising the metal complex, or the adsorbent material, storage material, or separation material of the present invention into a honeycomb shape. "Honeycomb shape" as mentioned in the present invention refers to a shape of continuous hollow polygonal columns with a hexagonal cross section, as well as a square, sine-wave, or roll cross section; or to a shape of continuous hollow cylindrical columns, such as cylinders. For example, sheets are formed into a sine-wave honeycomb shape in the following manner. First, a sheet is passed through shaping rolls to form a wave-shaped sheet, and a flat sheet is bonded to one or both sides of the wave-shaped sheet. These sheets are laminated to form a sine-wave honeycomb filter. It is common to secure the sheets with an adhesive that is put on the top of the wave shapes. However, when wave-shaped sheets comprising the metal complex, etc. of the present invention are laminated, a flat sheet placed between the wave-shaped sheets is necessarily secured, and so an adhesive is not necessarily used. When an adhesive is used, one that does not impair the adsorption performance of the sheets must be used. Usable adhesives are, for example, corn starch, vinyl acetate resin, and acrylic resin. The gas adsorption performance of the wave-shaped sheet can be enhanced by reducing the adhesion pitch of the sheet and lowering the thread height of the sheet. The pitch is preferably 0.5 to 8 mm, and the thread height is preferably 0.4 to 5 mm.

By taking advantage of its storage performance, the metal complex of the present invention (or the adsorbent material of the present invention) can be used in gas storage devices. One example of the gas storage devices is a gas storage device that comprises a pressure-resistant container that can be hermetically sealed and has an inlet and outlet for gas, wherein the pressure-resistant container has a gas storage space, and wherein the adsorbent material comprising the metal complex of the present invention is placed in the gas storage space. A desired gas is stored in the gas storage device by compressing the gas into the gas storage device so that the gas is adsorbed by the storage material placed in the device. The gas is taken out from the gas storage device by opening a pressure valve to reduce the internal pressure in the pressure-resistant container, thereby desorbing the gas. When the storage material is placed in the gas storage space, powders of the metal complex of the present invention can be used. In terms of handling properties, etc., pellets obtained by molding the metal complex of the present invention may be used.

Figure 3:
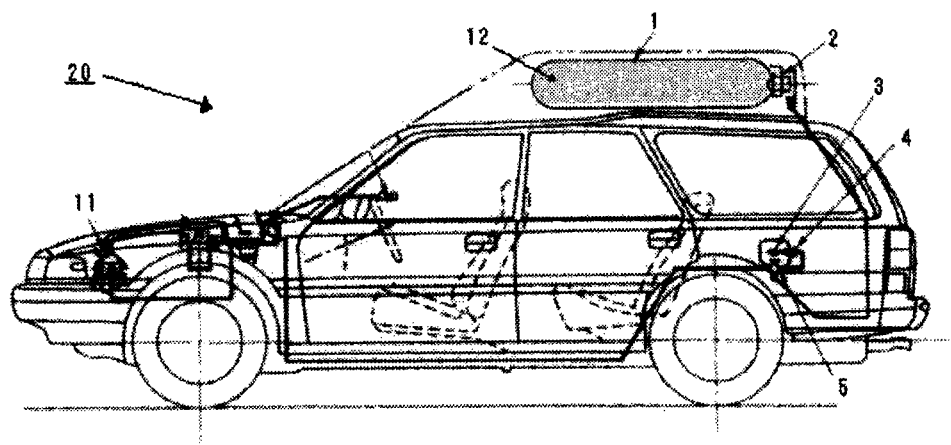
FIG. 3 is a conceptual diagram illustrating a gaseous-fuel vehicle comprising a gas storage device.

The gas storage device, as described above, can store fuel gas in a gas storage space, and can be suitably used as a fuel tank of, for example, a gaseous-fuel vehicle. FIG. 3 shows an example of a gaseous-fuel vehicle comprising the gas storage device of the present invention. The gaseous-fuel vehicle 20 comprises as a fuel tank 1, the above gas storage device, in which the metal complex of the present invention is placed, and also comprises an engine 11 as an internal combustion engine that receives natural gas stored in the fuel tank 1 and mixes the natural gas with oxygen-containing gas for combustion (e.g., air), thereby obtaining running drive force by combustion of the gas mixture. The fuel tank 1 is provided with at an outlet and inlet, a pressure control valve 2 that composes a hermetically sealing structure and that can maintain the gas inside under pressurized conditions, and the pressure control valve 2 is connected to a gas filler port 3, which is used as a port through which gas to be stored can enter and exit via a gas supply channel. Additionally, to stably supply fuel (natural gas), a nonreturn valve 4 and a three-way valve 5 are provided on a gas transfer channel. The nonreturn valve 4 is disposed between the gas filler port and the pressure control valve 2. The three-way valve 5 is disposed at a branch point between the gas supply channel, which connects the pressure control valve 2 and the gas filler port 3, and the gas transfer channel, which connects the pressure control valve 2 and the engine 11, to control gas flow at the branch point. The fuel tank 1 is filled with fuel (natural gas) in a pressurized state at a gas station. The fuel tank 1 is internally provided with a storage material 12 comprising the metal complex of the present invention. The storage material 12 adsorbs the natural gas (e.g., gas comprising methane as a main component) at ordinary temperature under increased pressure. When the pressure control valve 2 is opened, the adsorbed gas is desorbed from the storage material 12 and transmitted to the engine side 11 such that the gas is combusted to generate running drive force.

The fuel tank 1, which is internally provided with the storage material 12 comprising the metal complex of the present invention, has higher gas compressibility relative to the apparent pressure, compared to a fuel tank without the storage material. The thickness of the tank can be thereby reduced, and the weight of the entire gas storage device can also be reduced, which is advantageous, for example, for gaseous fuel vehicles. Additionally, the fuel tank 1 is generally maintained at ordinary temperature without cooling. When the temperature increases, e.g., during summer, the temperature of the tank becomes relatively high. The storage material of the present invention is able to maintain its high storage ability in such a high temperature range (about 298 to 333 K) and is therefore useful.

The separation method comprises a step of bringing a gas and the metal complex of the present invention (or the separation material of the present invention) into contact with each other under a condition that enables the gas to be adsorbed to the metal complex. The condition, i.e., the adsorption pressure and the adsorption temperature that enable the gas to be adsorbed to the metal complex can be suitably set according to the type of the material to be adsorbed. For example, the adsorption pressure is preferably 0.01 to 10 MPa, and more preferably 0.1 to 3.5 MPa. The adsorption temperature is preferably 195 to 343 K, and more preferably 273 to 313 K.

The pressure swing adsorption process or the temperature swing adsorption process may be used as the separation method. When performing the pressure swing adsorption process as the separation method, the separation method further comprises a step of increasing the pressure from an adsorption pressure to a pressure enabling the gas to be desorbed from the metal complex. The desorption pressure may be suitably set according to the type of the material to be adsorbed. For example, the desorption pressure is preferably 0.005 to 2 MPa, and more preferably 0.01 to 0.1 MPa. When performing the temperature swing adsorption process as the separation method, the separation method further comprises a step of increasing the temperature from an adsorption temperature to a temperature enabling the gas to be desorbed from the metal complex. The desorption temperature can be suitably set according to the type of the material to be adsorbed. For example, desorption temperature is preferably 303 to 473 K, and more preferably 313 to 373 K.

When performing the pressure swing adsorption process or the temperature swing adsorption process as the separation method, the step of bringing the gas to be in contact with the metal complex and the step of changing the pressure or the temperature that enables the gas to be desorbed from the metal complex may be appropriately repeated.

EXAMPLES

The present invention will hereinafter be described specifically by using examples. It should be borne in mind, however, that the invention is not limited to or limited by these examples. The analysis and evaluation in the following Examples and Comparative Examples were conducted as described below.
(1) Powder X-Ray Diffraction Pattern Measurement The powder X-ray diffraction pattern was measured using an X-ray diffractometer based on the symmetric reflection method while scanning at a scanning rate of 1°/min within a diffraction angle (2θ) range of from 5 to 50°. Details of the analysis conditions are shown below.
Analysis Conditions
Apparatus: Smart Lab produced by Rigaku Corporation
X-ray source: Cu Kα (λ=1.5418 Å) 45 kV 200 mA
Goniometer: Vertical Goniometer
Detector: D/teX Ultra
Step width: 0.02°
Slit: Divergence slit=2/3°
  Receiving slit=0.3 mm
  Scattering slit=2/3°
(2) Quantification of $C_1$ or $C_2$ Aliphatic Monocarboxylic Acid Compound The metal complex was dissolved in a deuterated solvent to perform $^1$H NMR measurement. The $C_1$ or $C_2$ aliphatic monocarboxylic acid compound was quantified from the integrated ratio of the resulting spectrum. Details of the analysis conditions are shown below.
Analysis Conditions
Apparatus: Advance 600 produced by Bruker Biospin K.K.
Resonance frequency: 600 MHz
Measurement solvent: Deuterated ammonia water or mixed solvent of deuterated ammonia water and deuterated trifluoroacetic acid
Standard substance: Sodium 3-(trimethylsilyl)propanoate-$d_4$
Measurement temperature: 298 K
(3) Observation Using SEM The metal complex obtained after conduction treatment was observed using a scanning electron microscope. Details of the analysis conditions are shown below.
Analysis Conditions
Apparatus: S-3000N produced by Hitachi High Technologies Corporation
Filament: Tungsten hairpin
Accelerating voltage: 10.0 kV
(4) Measurement of Adsorption Isotherm or Adsorption and Desorption Isotherms The amounts of gas adsorbed and desorbed were measured according to the volumetric method by using a high-pressure gas adsorption measuring instrument to plot adsorption and desorption isotherms (in accordance with JIS Z8831-2). Before the measurement, the sample was dried at 373 K and 0.5 Pa for 5 hours to remove adsorbed water and the like. The following are details of the analysis conditions.
Analysis Conditions
Apparatus: BELSORP-HP produced by Bel Japan, Inc.
Equilibrium waiting time: 500 s
(5) Water Vapor Exposure Test Using the Environmental test chamber PL-2KP produced by Espec Corporation, the metal complexes obtained in Synthesis Examples and Comparative Synthesis Examples were placed under an atmosphere, i.e., at 353 K and a relative humidity of 80% to perform a water vapor exposure test. The results were used as an index to evaluate water resistance. The sampling was performed 8 hours, 24 hours, and 48 hours after the start of the water vapor exposure, and the amount of carbon dioxide adsorbed at 273 K was measured according to the volumetric method to plot an adsorption isotherm in the same manner as the above.
(6) Measurement of Breakthrough Curve A pressure-resistant glass container with a volume of 10 mL connected with a cylinder via a stainless steel tube equipped with a gas flowmeter and valves was prepared. The measurement was conducted by placing a sample into the pressure-resistant glass container, drying the sample at 373 K and 7 Pa for 3 hours to remove the adsorbed water or the like, and passing a gas mixture through the container. During the measurement, outlet gas was sampled every 2 minutes and analyzed by gas chromatography to calculate the composition of the outlet gas. (The composition of inlet gas was measured beforehand by gas chromatography.) The details of analysis conditions are described below.
Analysis Conditions
Apparatus: GC-14B produced by Shimadzu Corporation
Column: Unibeads C 60/80 produced by GL Sciences, Inc.
Column temperature: 200° C.
Carrier gas: Helium
Injection rate: 1.0 mL
Detector: TCD Synthesis Example 1

Under nitrogen atmosphere, 5.86 g (23.5 mmol) of copper sulfate pentahydrate, 3.90 g (23.5 mmol) of terephthalic acid, and 32.4 g (704 mmol) of formic acid were dissolved in 3,750 mL of methanol. The mixture was stirred at 313 K for 24 hours. After collecting the precipitated metal complex by suction filtration, the metal complex was washed three times with methanol to isolate an intermediate. Subsequently, the isolated intermediate was dispersed in methanol (2,000 mL) under nitrogen atmosphere, and 1.83 g (11.7 mmol) of 4,4'-bipyridyl was added thereto. The mixture was stirred at 298 K for 3 hours, during which the reaction solution remained suspended. After collecting the metal complex by suction filtration, the metal complex was washed three times with methanol. Subsequently, the mixture was dried at 373 K and 50 Pa for 8 hours, thereby obtaining 1.79 g of the target metal complex.

Figure 4:
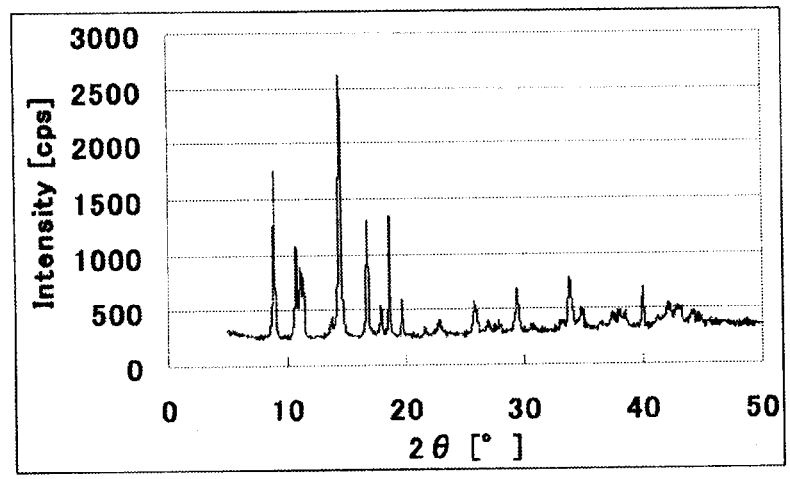
FIG. 4 shows a powder X-ray diffraction pattern of a metal complex obtained in Synthesis Example 1.

The powder X-ray diffraction pattern of the resulting metal complex is shown in FIG. 4. The results of the powder X-ray crystal structure analysis reveals that the resulting metal complex has a structure in which two jungle-gym-type frameworks are interpenetrated into each other. The powder X-ray crystal structure analysis results are shown below.
Triclinic (P-1)
a=7.87355 Å
b=8.94070 Å
c=10.79101 Å
α=67.14528°
β=80.73986°
γ=79.31579°
$R_{wp}$=2.30%
$R_I$=4.96%

Figure 5:
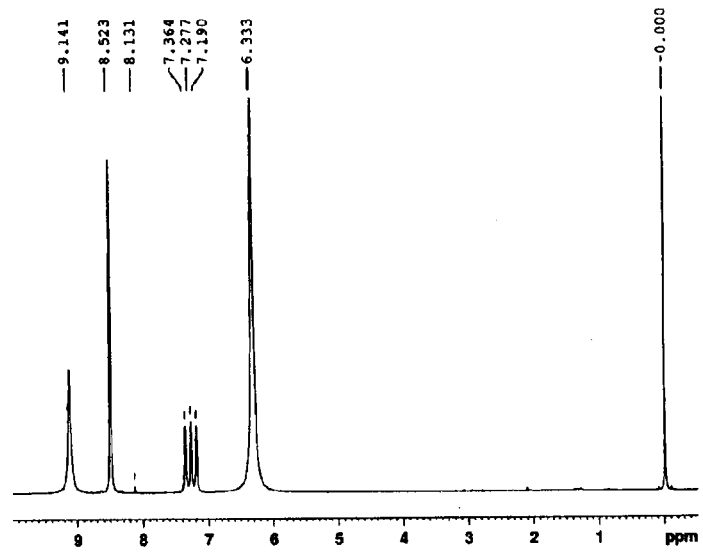
FIG. 5 shows a $^1$H-NMR spectrum measured by dissolving the metal complex obtained in Synthesis Example 1 in a mixed solution of deuterated ammonia water and deuterated trifluoroacetic acid.

10 mg of the resulting metal complex was dissolved in a mixed solvent of deuterated ammonia water (700 mg) and deuterated trifluoroacetic acid (1,106 mg) to perform $^1$H NMR measurement. The resulting spectrum is shown in FIG. 5. As a result of spectrum analysis, the peak integral value attributed to a proton of formic acid at 8.131 ppm (s, 1H) was 4.587 when the total of the peak integral value attributed to protons at positions 2, 6, 2' and 6' of the 4,4'-bipyridil at 9.141 ppm (s, 4H) and the peak integral value attributed to protons at positions 3, 5, 3', and 5' of the 4,4'-bipyridil at 8.523 ppm (s, 4H) was taken as 1,000. This indicates that the molar ratio of the 4,4'-bipyridyl and formic acid contained in the metal complex is such that 4,4'-bipyridyl:formic acid=27:1.

Figure 6:
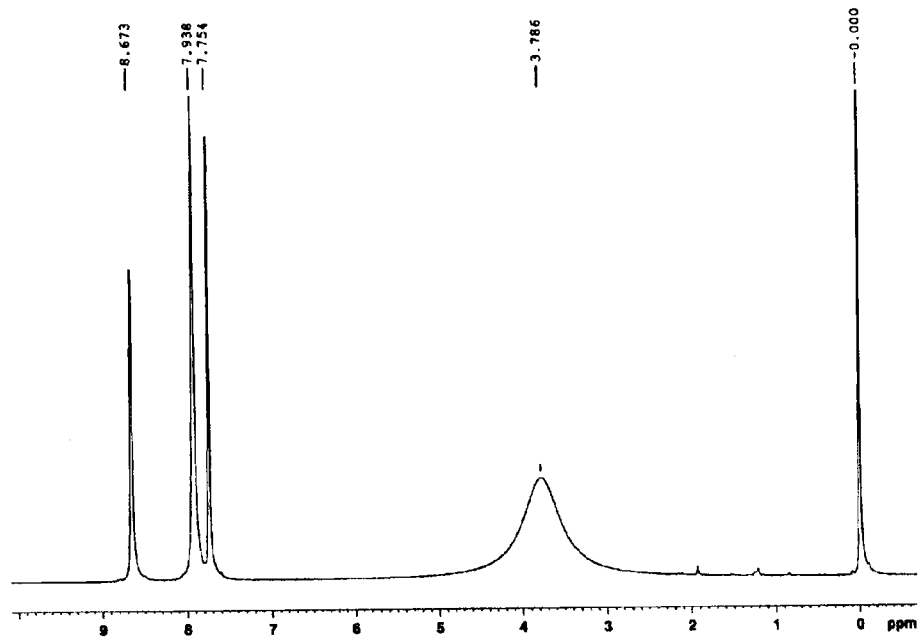
FIG. 6 shows a $^1$H-NMR spectrum measured by dissolving the metal complex obtained in Synthesis Example 1 in deuterated ammonia water.

10 mg of the resulting metal complex was dissolved in deuterated ammonia water (700 mg) to perform $^1$H NMR measurement. The resulting spectrum is shown in FIG. 6. As a result of spectrum analysis, the peak integral value attributed to protons at positions 2, 6, 2', and 6' of the 4,4'-bipyridil at 8.673 ppm (s, 4H) was 492 when the peak integral value attributed to protons at positions 2, 3, 5, and 6 of the terephthalic acid at 7.938 ppm (s, 4H) was taken as 1,000. This indicates that the molar ratio of the terephthalic acid to 4,4'-bipyridyl contained in the metal complex is such that terephthalic acid: 4,4'-bipyridyl=2.03:1. In FIG. 6, the broad signal around at 3.8 ppm is attributed to water. According to the above results, the molar ratio of the terephthalic acid to formic acid contained in the metal complex was calculated such that terephthalic acid:formic acid=54:1

The results of the powder X-ray crystal structure analysis and $^1$H NMR measurement reveal that the composition formula of the resulting metal complex is $[Cu_2(C_8H_4O_4)_{2-x}(C_{10}H_8N_2)(HCOO)_x]_n$ (x=0.036). n is a positive integer. Since the value x was small, the theoretical yield was calculated based on the molecular weight of the compound represented by $[Cu_2(C_8H_4O_4)_2(C_{10}H_8N_2)]_n$ (copper:terephthalic acid:4,4'-bipyridyl=2:2:1). Consequently, the yield of the resulting metal complex was 25%.

Figure 7:
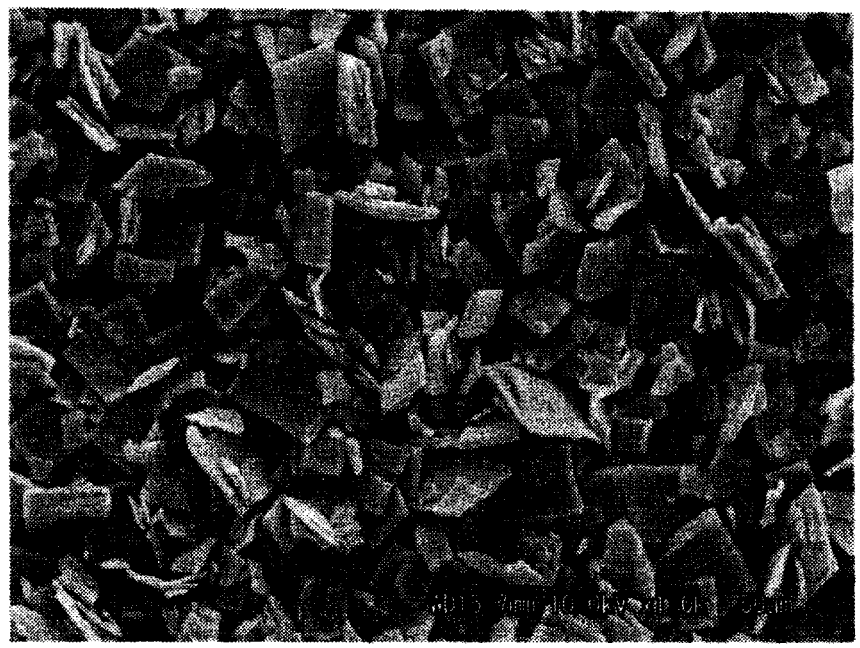
FIG. 7 is an SEM image of a metal complex obtained in Synthesis Example 1.

The SEM image of the resulting metal complex is shown in FIG. 7 (magnification: 1000×).

The metal complex (0.96 g) of Synthesis Example 1 and a polytetrafluoroethylene polymer (0.24 g) (Teflon®, produced by Dupont-Mitsui Fluorochemicals Co., Ltd.) were kneaded in a mortar, thereby obtaining a composition. The resulting composition was placed in a mill (inner diameter: 3.0 mm; length: 15 mm), and subjected to tablet compression at 200 kgf (about 1.96 kN) using a simple tablet press (HANDTAB-100, produced by Ichihashi Seiki Co., Ltd.) to obtain a pellet-shaped molded product having a diameter of 3.0 mm and a length of 15 mm.

Synthesis Example 2

Under nitrogen atmosphere, 5.86 g (23.5 mmol) of copper sulfate pentahydrate, 3.90 g (23.5 mmol) of terephthalic acid, and 42.3 g (704 mmol) of acetic acid were dissolved in 3,750 mL of methanol. The mixture was stirred at 313 K for 24 hours. After collecting the precipitated metal complex by suction filtration, the metal complex was washed three times with methanol to isolate an intermediate. Subsequently, the isolated intermediate was dispersed in methanol (2,000 mL) under nitrogen atmosphere, and 1.83 g (11.7 mmol) of 4,4'-bipyridyl was added thereto. The mixture was stirred at 298 K for 3 hours, during which the reaction solution remained suspended. After collecting the metal complex by suction filtration, the metal complex was washed three times with methanol. Subsequently, the mixture was dried at 373 K and 50 Pa for 8 hours, thereby obtaining 1.55 g of the target metal complex.

Figure 8:
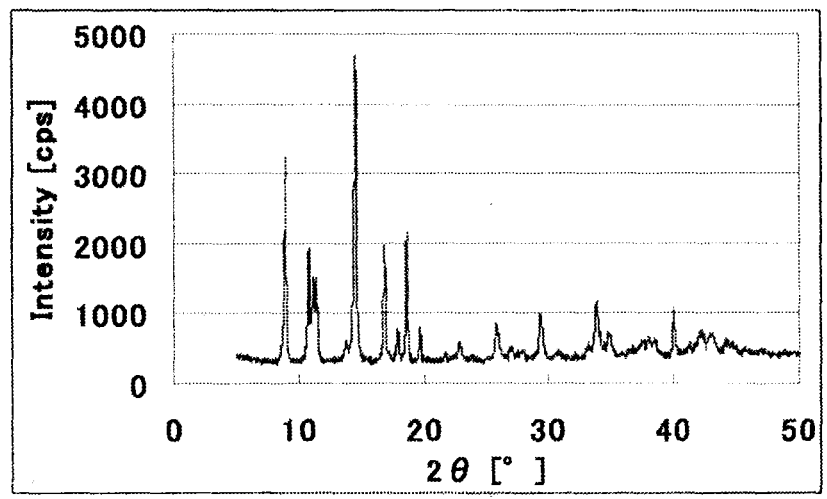
FIG. 8 shows a powder X-ray diffraction pattern of a metal complex obtained in Synthesis Example 2.

The powder X-ray diffraction pattern of the resulting metal complex is shown in FIG. 8. The results of the powder X-ray crystal structure analysis reveal that the resulting metal complex has a structure in which two jungle-gym-type frameworks are interpenetrated into each other, as in the metal complex obtained in Synthesis Example 1.

Figure 9:
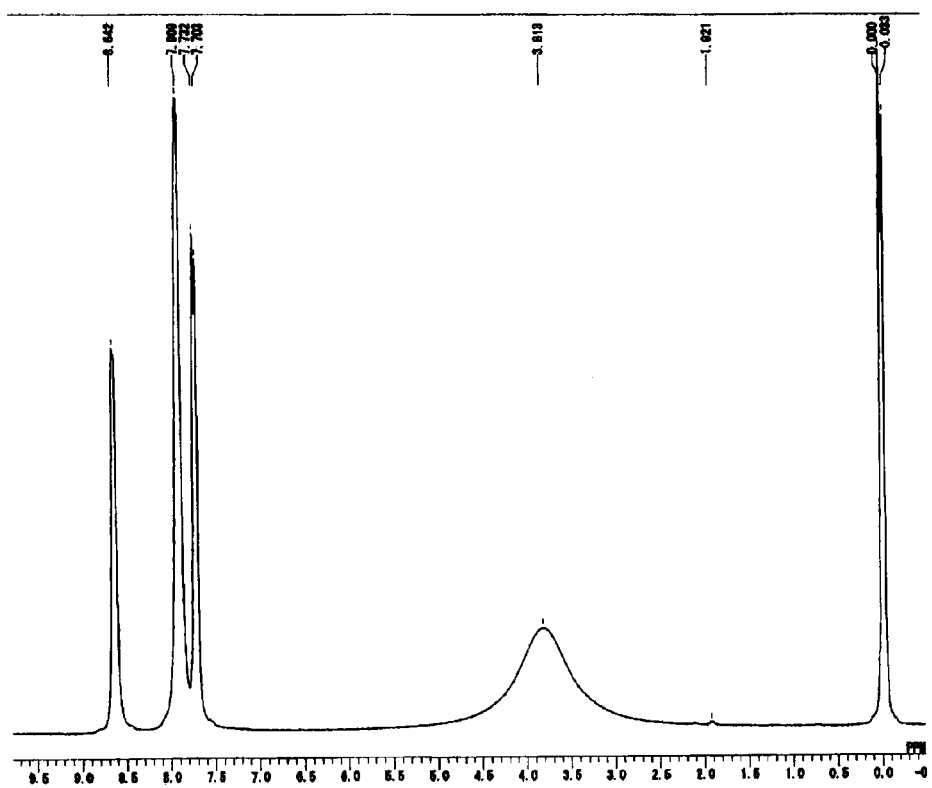
FIG. 9 shows a $^1$H-NMR spectrum measured by dissolving the metal complex obtained in Synthesis Example 2 in deuterated ammonia water.

10 mg of the resulting metal complex was dissolved in 700 mg of deuterated ammonia water (containing 0.4 wt % sodium 3-(trimethylsilyl)propanoate-d$_4$ as a standard substance) to perform $^1$H NMR measurement. The resulting spectrum is shown in FIG. 9. As a result of spectrum analysis, the peak integral value attributed to protons at position 1 of the acetic acid at 1.921 ppm (s, 4H) was 30.080 when the peak integral value attributed to protons at positions 2, 3, 5, and 6 of the terephthalic acid at 7.909 ppm (s, 4H) was taken as 1,000. This indicates that the molar ratio of the terephthalic acid to acetic acid contained in the metal complex is such that terephthalic acid:acetic acid=208:1. In FIG. 9, the broad signal around 3.8 ppm is attributed to water.

The results of the powder X-ray crystal structure analysis and $^1$H NMR measurement reveal that the composition formula of the resulting metal complex is $[Cu_2(C_8H_4O_4)_{2-x}(C_{10}H_8N_2)(CH_3COO)_x]_n$ (x=0.0096). n is a positive integer. Since the value x was small, the theoretical yield was calculated based on the molecular weight of the compound represented by $[Cu_2(C_8H_4O_4)_2(C_{10}H_8N_2)]_n$ (copper:terephthalic acid:4,4'-bipyridyl=2:2:1). Consequently, the yield of the resulting metal complex was 22%.

Figure 10:
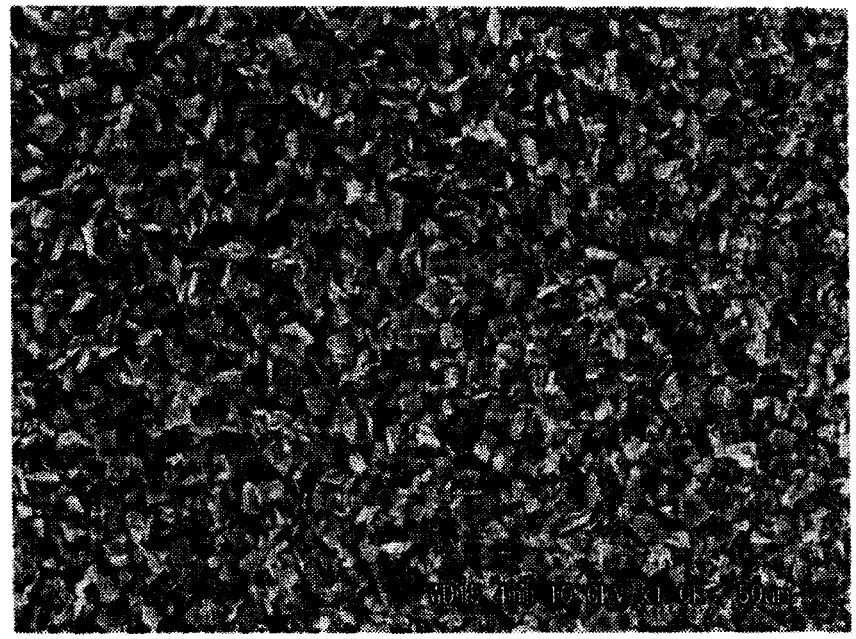
FIG. 10 is an SEM image of a metal complex obtained in Synthesis Example 2.

The SEM image of the resulting metal complex is shown in FIG. 10 (magnification: 1000×).

Synthesis Example 3

Under nitrogen atmosphere, 2.12 g (10.6 mmol) of copper acetate monohydrate in which acetic acid was used as a counter anion, and 1.76 g (10.6 mmol) of terephthalic acid were dissolved in 800 mL of methanol. The mixture was stirred at 333 K for 24 hours. After collecting the precipitated metal complex by suction filtration, the metal complex was washed three times with methanol to isolate an intermediate. Subsequently, the isolated intermediate was dispersed in methanol (900 mL) under nitrogen atmosphere, and 0.828 g (5.30 mmol) of 4,4'-bipyridyl was added thereto. The mixture was stirred at 313 K for 3 hours, during which the reaction solution remained suspended. After collecting the metal complex by suction filtration, the metal complex was washed three times with methanol. Subsequently, the mixture was dried at 373 K and 50 Pa for 8 hours, thereby obtaining 2.76 g of the target metal complex.

Figure 11:
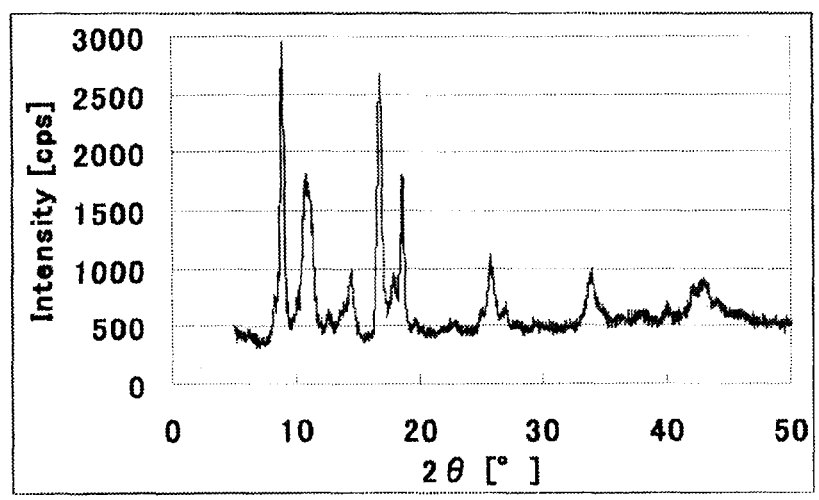
FIG. 11 shows a powder X-ray diffraction pattern of a metal complex obtained in Synthesis Example 3.

The powder X-ray diffraction pattern of the resulting metal complex is shown in FIG. 11. The results of the powder X-ray crystal structure analysis reveals that the resulting metal complex has a structure in which two jungle-gym-type frameworks are interpenetrated into each other, as in the metal complex obtained in Synthesis Example 1.

$^1$H NMR measurement was conducted in the same manner as in Synthesis Example 2. The results indicate that the molar ratio of the terephthalic acid to acetic acid is such that terephthalic acid:acetic acid=78:1.

The yield of the resulting metal complex calculated in the same manner as in Synthesis Example 2 was 85%.

Figure 12:
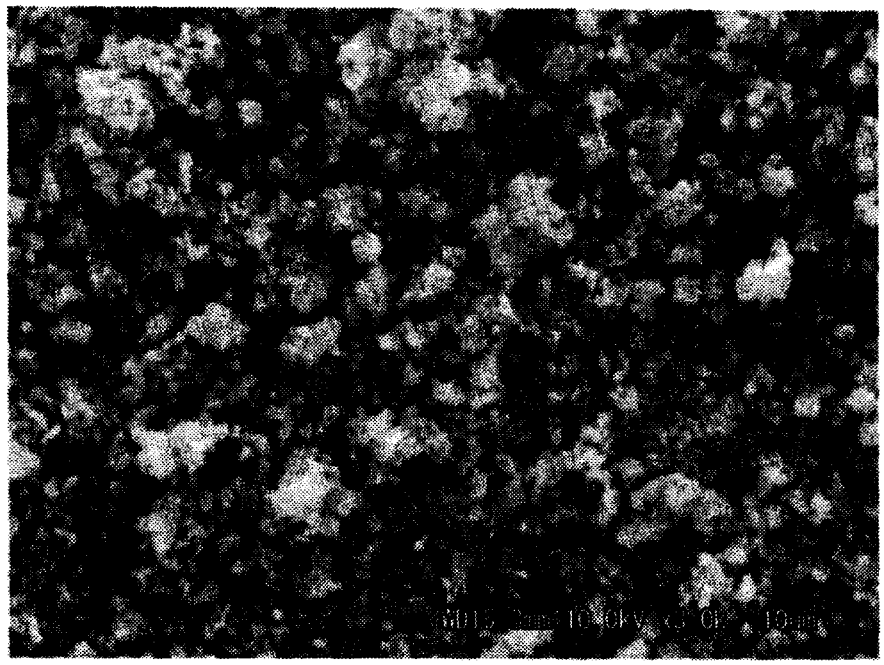
FIG. 12 is an SEM image of a metal complex obtained in Synthesis Example 3.

The SEM image of the resulting metal complex is shown in FIG. 12 (magnification: 3000×).

Comparison between FIGS. 10 and 12 reveals that the particle diameter of the metal complex changes depending on the amount of acetic acid added.

Comparative Synthesis Example 1

Under nitrogen atmosphere, 28.1 g (94.5 mmol) of zinc nitrate hexahydrate, 15.7 g (94.5 mmol) of terephthalic acid, and 7.39 g (47.3 mmol) of 4,4'-bipyridyl were dissolved in 8000 mL of mixed solvent comprising N,N-dimethylformamide and ethanol in a volume ratio of 1:1. The mixture was stirred at 363 K for 48 hours. After collecting the precipitated metal complex by suction filtration, the metal complex was washed three times with methanol. Subsequently, the resultant was dried at 373 K and 50 Pa for 8 hours, thereby obtaining 27.5 g (yield 95%) of the target metal complex.

Figure 13:
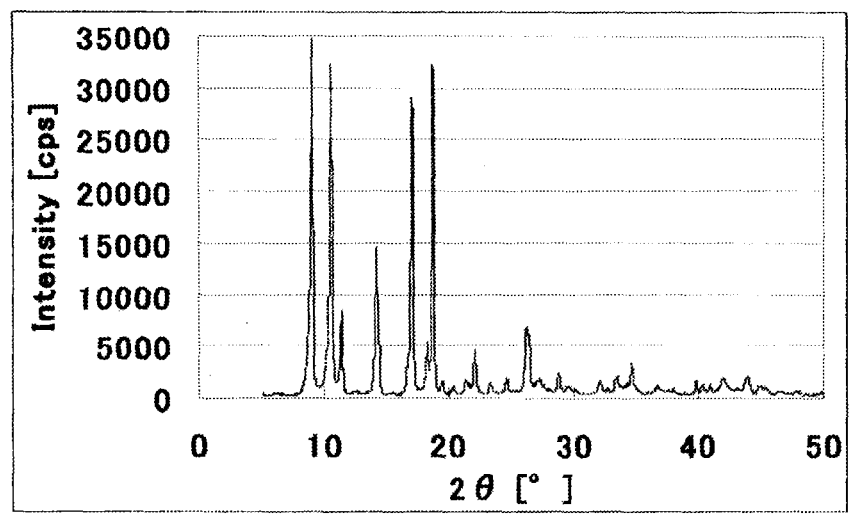
FIG. 13 shows a powder X-ray diffraction pattern of a metal complex obtained in Comparative Synthesis Example 1.

The powder X-ray diffraction pattern of the resulting metal complex is shown in FIG. 13. Comparison from the simulation pattern obtained based on the structure analysis results of the separately synthesized single crystal reveals that the resulting metal complex has a structure in which two jungle-gym-type frameworks are interpenetrated into each other. The single crystal structure analysis results are shown below.
Triclinic (P-1)
a=7.7911 (13) Å
b=9.2984 (18) Å
c=10.6284 (19) Å
α=65.320 (7)°
β=86.199 (7)°
γ=78.145 (7)°
V=684.6 (2) Å$^3$
Z=2
R=0.0325
$R_w$=0.0836

Comparative Synthesis Example 2

Figure 14:
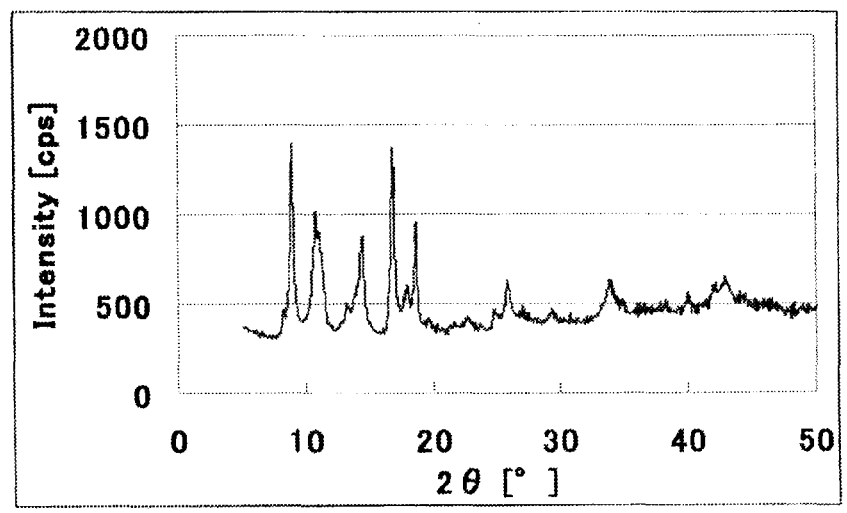
FIG. 14 shows a powder X-ray diffraction pattern of a metal complex obtained in Comparative Synthesis Example 2.

Under nitrogen atmosphere, 21.8 g (109 mmol) of copper acetate monohydrate, 18.2 g (109 mmol) of terephthalic acid, and 32.9 g (547 mmol) of acetic acid were dissolved in 200 mL of methanol. The mixture was stirred at 333 K for 48 hours. After collecting the precipitated metal complex by suction filtration, the metal complex was washed 10 times with methanol to isolate an intermediate. Subsequently, the isolated intermediate was dispersed in methanol (133 mL) under nitrogen atmosphere, and 8.54 g (54.7 mmol) of 4,4'-bipyridyl was added thereto. The mixture was stirred at 313 K for 3 hours, during which the reaction solution remained suspended. After collecting the metal complex by suction filtration, the metal complex was washed 5 times with methanol. Subsequently, the mixture was dried at 373 K and 50 Pa for 8 hours, thereby obtaining 29.9 g of the target metal complex. The powder X-ray diffraction pattern of the resulting metal complex is shown in FIG. 14. The results of the powder X-ray crystal structure analysis reveals that the resulting metal complex has a structure in which two jungle-gym-type frameworks are interpenetrated into each other, as in the metal complex obtained in Synthesis Example 1.

$^1$H NMR measurement was conducted in the same manner as in Synthesis Example 2. The results indicate that the molar ratio of the terephthalic acid to acetic acid is such that terephthalic acid compound:acetic acid=5.4:1.

The results of the powder X-ray crystal structure analysis and $^1$H NMR measurement reveal that the composition formula of the resulting metal complex is $[Cu_2(C_8H_4O_4)_{2-x}(C_{10}H_8N_2)(CH_3COO)_x]_n$ (x=0.31). n is a positive integer. The theoretical yield was calculated based on the molecular weight of the compound represented by $[Cu_2(C_8H_4O_4)_{1.69}(C_{10}H_8N_2)(CH_3COO)\ 0\ 0.31]_n$ (copper:terephthalic acid:4,4'-bipyridyl:acetic acid=2:1.69:1:0.31). Consequently, the yield of the resulting metal complex was 94%.

Figure 15:
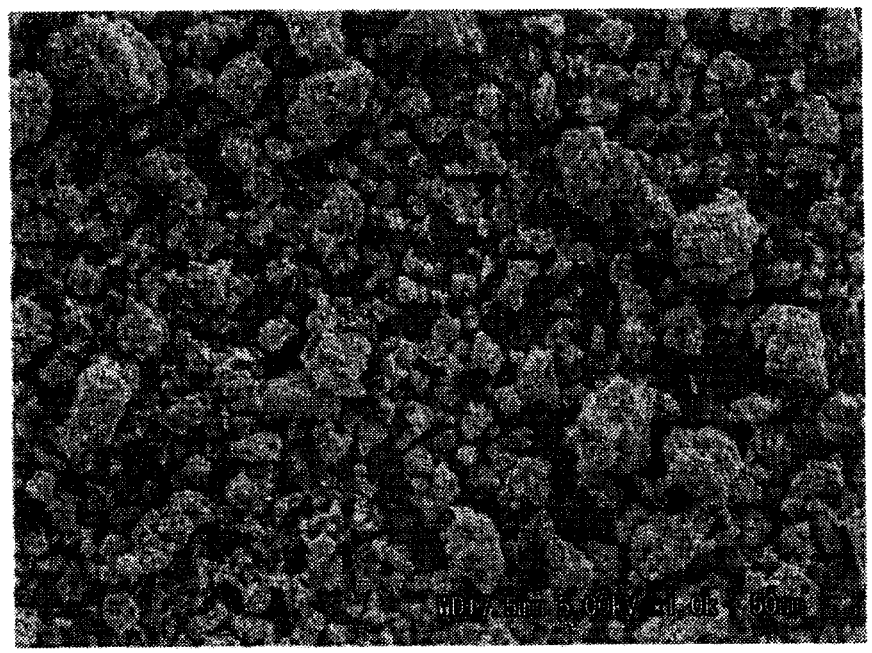
FIG. 15 is an SEM image of a metal complex obtained in Comparative Synthesis Example 2.

The SEM image of the resulting metal complex is shown in FIG. 15 (magnification: 1000×).

Synthesis Comparative Example 3

Under nitrogen atmosphere, 5.86 g (23.5 mmol) of copper sulfate pentahydrate, 3.90 g (23.5 mmol) of terephthalic acid, and 85.9 g (704 mmol) of benzoic acid were dissolved in 3.750 mL of methanol. The mixture was stirred at 313 K for 24 hours; however, the metal complex was not precipitated and the solution remained homogeneous.

Table 1 shows the results of the metal complexes obtained in Synthesis Examples 1 to 3 and Comparative Synthesis Examples 1 to 3.

TABLE 1

| | Metal complex | | Composition ratio in metal complex* | | Powder X-ray diffraction | SEM image |
|---|---|---|---|---|---|---|
| | Multivalent carboxylic acid | Monocarboxylic acid | Multivalent carboxylic acid | Monocarboxylic acid | | |
| Synthesis Example 1 | Terephthalic acid | Formic acid | 54 | 1 | FIG. 4 | FIG. 7 |
| Synthesis Example 2 | Terephthalic acid | Acetic acid | 208 | 1 | FIG. 8 | FIG. 10 |
| Synthesis Example 3 | Terephthalic acid | Acetic acid | 78 | 1 | FIG. 11 | FIG. 12 |
| Comparative Synthesis Example 1 | Terephthalic acid | — | 100 | 0 | FIG. 13 | — |
| Comparative Synthesis Example 2 | Terephthalic acid | Acetic acid | 5.4 | 1 | FIG. 14 | FIG. 15 |
| Comparative Synthesis Example 3 | Terephthalic acid | Benzoic acid | No metal complex was obtained. | | | |

*Molar ratio

Example 1

Figure 16:
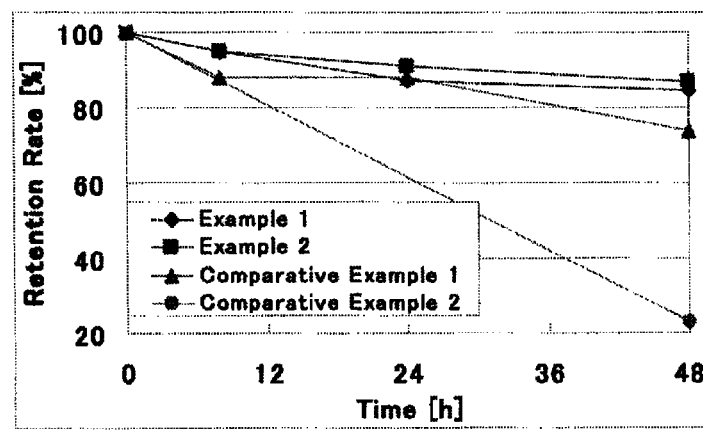
FIG. 16 shows the water resistance evaluation results of metal complexes obtained in Synthesis Examples 1 and 2 and Comparative Synthesis Examples 1 and 2.

A water vapor exposure test was performed on the metal complex obtained in Synthesis Example 1. The equilibrium adsorption amount of carbon dioxide at 0.92 MPa was calculated from the obtained adsorption isotherm, and the change in retention rate was plotted. The results are shown in FIG. 16 (Example 1).

Example 2

A water vapor exposure test was performed on the metal complex obtained in Synthesis Example 2. The equilibrium adsorption amount of carbon dioxide at 0.92 MPa was calculated from the obtained adsorption isotherm, and the change in retention rate was plotted. The results are shown in FIG. 16 (Example 2).

Comparative Example 1

A water vapor exposure test was performed on the metal complex obtained in Comparative Synthesis Example 1. The equilibrium adsorption amount of carbon dioxide at 0.92 MPa was calculated from the obtained adsorption isotherm, and the change in retention rate was plotted. The results are shown in FIG. 16 (Comparative Example 1).

Comparative Example 2

A water vapor exposure test was performed on the metal complex obtained in Comparative Synthesis Example 2. The equilibrium adsorption amount of carbon dioxide at 0.92 MPa was calculated from the obtained adsorption isotherm, and the change in retention rate was plotted. The results are shown in FIG. 16 (Comparative Example 2).

Table 2 shows the retention rates of Examples 1 and 2 and Comparative Examples 1 and 2 obtained 48 hours after exposure to water vapor. Each value indicates an equilibrium adsorption amount based on the equilibrium adsorption amount (100%) of carbon dioxide on the metal complex before exposure to water vapor at 0.92 MPa. The higher the value, the less the effect due to exposure to water vapor, and the higher the water resistance.

TABLE 2

|  | Metal complex | Retention rate after 48 hours (%) |
|---|---|---|
| Example 1 | Synthesis Example 1 | 84.6 |
| Example 2 | Synthesis Example 2 | 86.7 |
| Comparative Example 1 | Comparative Synthesis Example 1 | 73.7 |
| Comparative Example 2 | Comparative Synthesis Example 2 | 22.9 |

FIG. 16 and Table 2 reveal that the metal complexes obtained in Synthesis Examples 1 and 2, which satisfy the constituent features of the present invention and have a $C_1$ or $C_2$ monocarboxylic acid compound, have a higher carbon dioxide equilibrium adsorption retention rate even under high temperature and high humidity, and less decrease in the retention rate over time. In contrast, the equilibrium adsorption retention rates of the metal complex obtained in Comparative Synthesis Example 1, which does not have a monocarboxylic acid compound, and of the metal complex of Comparative Synthesis Example 2, the monocarboxylic acid compound amount of which is outside the range of the present invention, were remarkably reduced over time under high temperature and high humidity. This clearly indicates that the metal complex of the present invention has excellent water resistance.

Example 3

Figure 17:
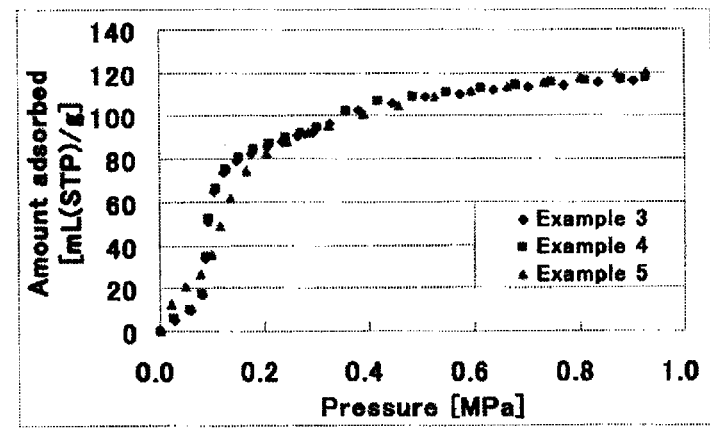
FIG. 17 shows adsorption isotherms of carbon dioxide on metal complexes obtained in Synthesis Examples 1, 2, and 3 at 273 K.

The amount of carbon dioxide adsorbed at 273 K by the metal complex obtained in Synthesis Example 1 was measured according to the volumetric method to plot an adsorption isotherm. The results are shown in FIG. 17 (Example 3).

Example 4

The amount of carbon dioxide adsorbed at 273 K by the metal complex obtained in Synthesis Example 2 was measured according to the volumetric method to plot an adsorption isotherm. The results are shown in FIG. 17 (Example 4).

Example 5

The amount of carbon dioxide adsorbed at 273 K by the metal complex obtained in Synthesis Example 3 was measured according to the volumetric method to plot an adsorption isotherm. The results are shown in FIG. 17 (Example 5).

FIG. 17 reveals that since the metal complexes obtained in Synthesis Examples 1, 2, and 3, which satisfy the constituent features of the present invention, adsorb carbon dioxide along with the increase in pressure, the metal complex of the present invention can be used as an adsorbent material for carbon dioxide. Further, comparison between Examples 4 and 5 reveals that the gas adsorption behavior of the metal complex changes depending on the amount of acetic acid added.

Example 6

The amount of ethylene adsorbed at 273 K by the metal complex obtained in Synthesis Example 1 was measured according to the volumetric method to plot an adsorption isotherm. The results are shown in FIG. 18.

Figure 18:
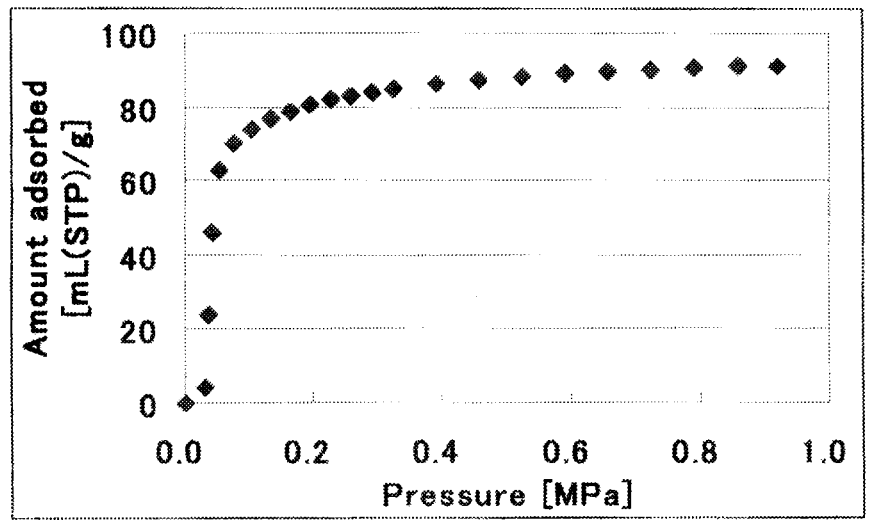
FIG. 18 shows an adsorption isotherm of ethylene on a metal complex obtained in Synthesis Example 1 at 273 K.

FIG. 18 reveals that since the metal complex obtained in Synthesis Example 1, which satisfies the constituent features of the present invention, adsorbs ethylene along with the increase in pressure, the metal complex of the present invention can be used as an adsorbent material for ethylene.

Example 7

The amount of argon adsorbed at 298 K by the metal complex obtained in Synthesis Example 2 was measured according to the volumetric method to plot an adsorption isotherm. The results are shown in FIG. 19.

Figure 19:
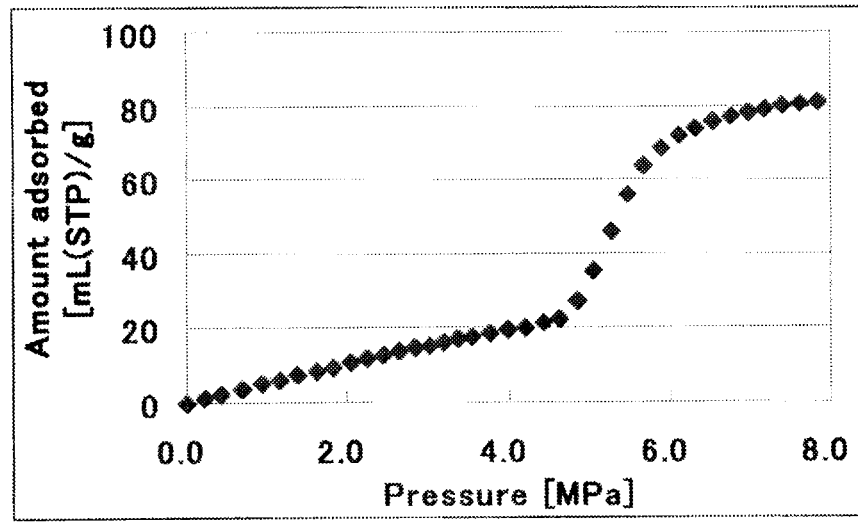
FIG. 19 shows an adsorption isotherm of argon on a metal complex obtained in Synthesis Example 2 at 298 K.

FIG. 19 reveals that since the metal complex obtained in Synthesis Example 2, which satisfies the constituent features of the present invention, adsorbs argon along with the increase in pressure, the metal complex of the present invention can be used as an adsorbent material for argon.

Example 8

The amounts of propane adsorbed and desorbed at 298 K by the metal complex obtained in Synthesis Example 1 were measured according to the volumetric method to plot adsorption and desorption isotherms. The results are shown in FIG. 20.

Figure 20:
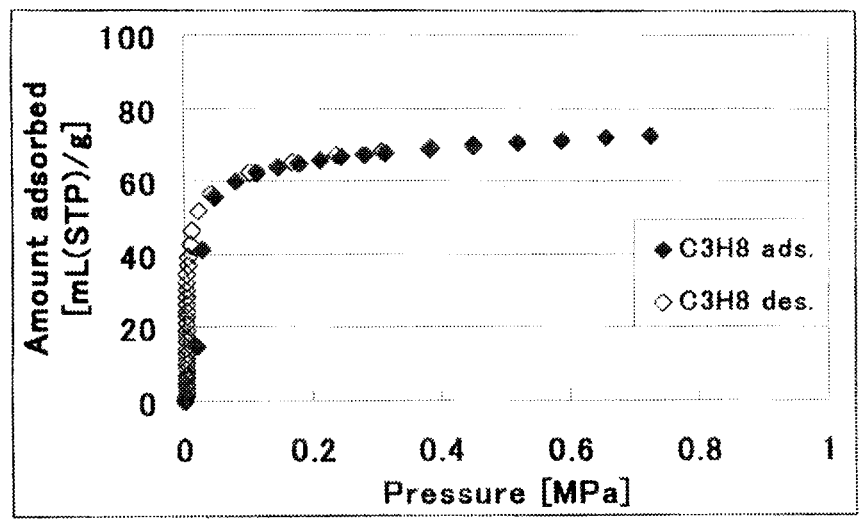
FIG. 20 shows adsorption and desorption isotherms of propane on a metal complex obtained in Synthesis Example 1 at 298 K.

FIG. 20 reveals that since the metal complex obtained in Synthesis Example 1, which satisfies the constituent features of the present invention, adsorbs propane along with the increase in pressure, and releases propane along with the decrease in pressure, the metal complex of the present invention can be used as a storage material for propane.

Example 9

The amounts of methane adsorbed and desorbed at 298 K by the metal complex obtained in Synthesis Example 1 were measured according to the volumetric method to plot adsorption and desorption isotherms. The results are shown in FIG. 21.

Figure 21:
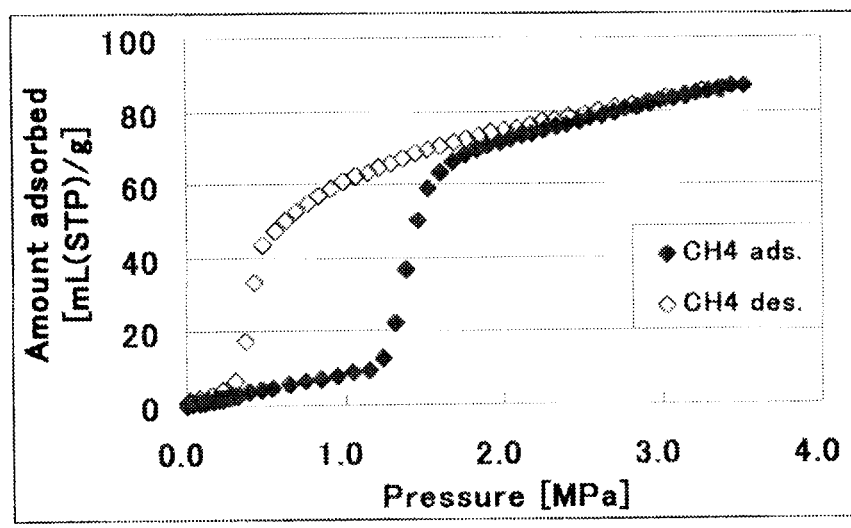
FIG. 21 shows adsorption and desorption isotherms of methane on a metal complex obtained in Synthesis Example 1 at 298 K.

FIG. 21 reveals that since the metal complex obtained in Synthesis Example 1, which satisfies the constituent features of the present invention, adsorbs methane along with the increase in pressure, and releases methane along with the decrease in pressure, the metal complex of the present invention can be used as a storage material for methane. Further, since the metal complex obtained in Synthesis Example 1 desorbs 95% or more of the adsorbed methane along with the decrease in pressure without decreasing the pressure to 0.1 Mpa or less, it is clear that the effective methane storage amount is large. Thus, the metal complex of the present invention is expected to be applied for fuel storage tanks of gaseous-fuel vehicles.

Example 10

The amounts of carbon dioxide adsorbed and desorbed at 293 K by the metal complex obtained in Synthesis Example 2 were measured according to the volumetric method to plot adsorption and desorption isotherms. The results are shown in FIG. 22.

Figure 22:
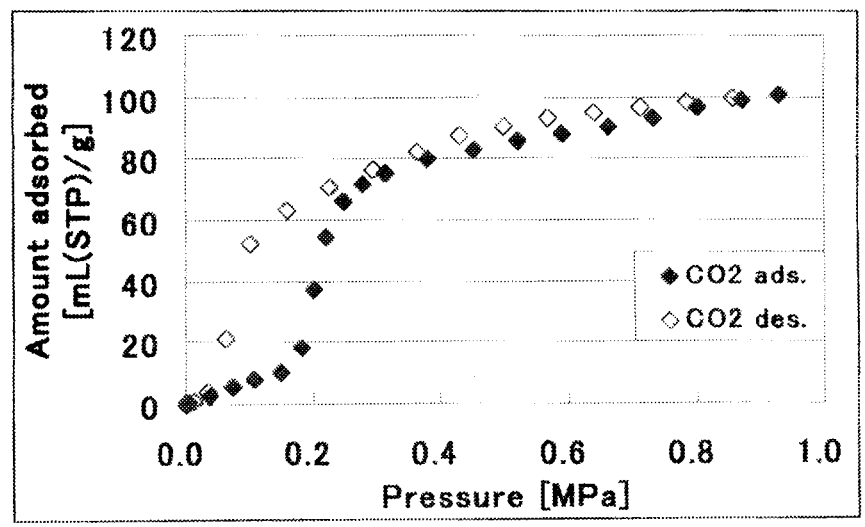
FIG. 22 shows adsorption and desorption isotherms of carbon dioxide on a metal complex obtained in Synthesis Example 2 at 293 K.

FIG. 22 reveals that since the metal complex obtained in Synthesis Example 2, which satisfies the constituent features of the present invention, adsorbs carbon dioxide along with the increase in pressure, and releases carbon dioxide along with the decrease in pressure, the metal complex of the present invention can be used as a storage material for carbon dioxide.

Example 11

The amounts of oxygen adsorbed and desorbed at 298 K by the metal complex obtained in Synthesis Example 2 were measured according to the volumetric method to plot adsorption and desorption isotherms. The results are shown in FIG. 23.

Figure 23:
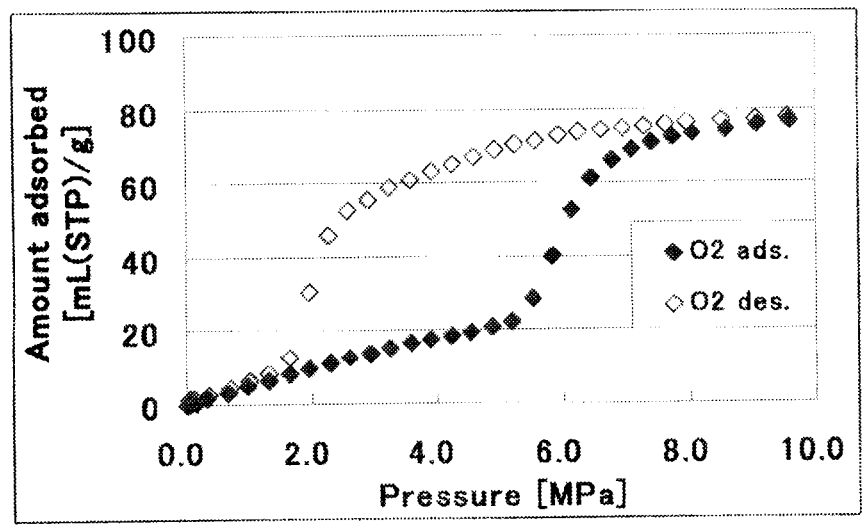
FIG. 23 shows adsorption and desorption isotherms of oxygen on a metal complex obtained in Synthesis Example 2 at 298 K.

FIG. 23 reveals that since the metal complex obtained in Synthesis Example 2, which satisfies the constituent features of the present invention, adsorbs oxygen along with the increase in pressure, and releases oxygen along with the decrease in pressure, the metal complex of the present invention can be used as a storage material for oxygen.

Example 12

The amounts of carbon dioxide and hydrogen adsorbed and desorbed at 313 K by the metal complex obtained in Synthesis Example 1 were measured according to the volumetric method to plot adsorption and desorption isotherms. The results are shown in FIG. 24.

Figure 24:
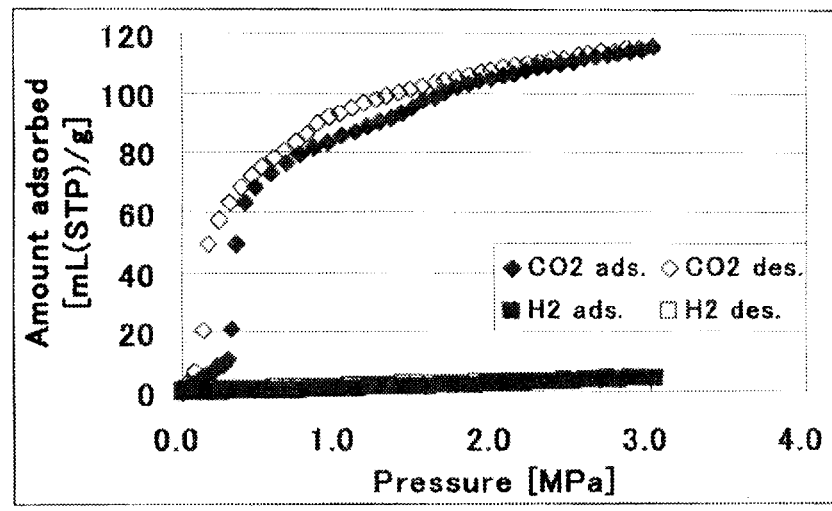
FIG. 24 shows adsorption and desorption isotherms of carbon dioxide and hydrogen on a metal complex obtained in Synthesis Example 1 at 313 K.

FIG. 24 reveals that since the metal complex obtained in Synthesis Example 1, which satisfies the constituent features of the present invention, selectively adsorbs carbon dioxide along with the increase in pressure, and releases carbon dioxide along with the decrease in pressure, the metal complex of the present invention can be used as a material for separating hydrogen and carbon dioxide.

Example 13

The amounts of methane and nitrogen adsorbed and desorbed at 298 K by the metal complex obtained in Synthesis Example 1 were measured according to the volumetric method to plot adsorption and desorption isotherms. The results are shown in FIG. 25.

Figure 25:
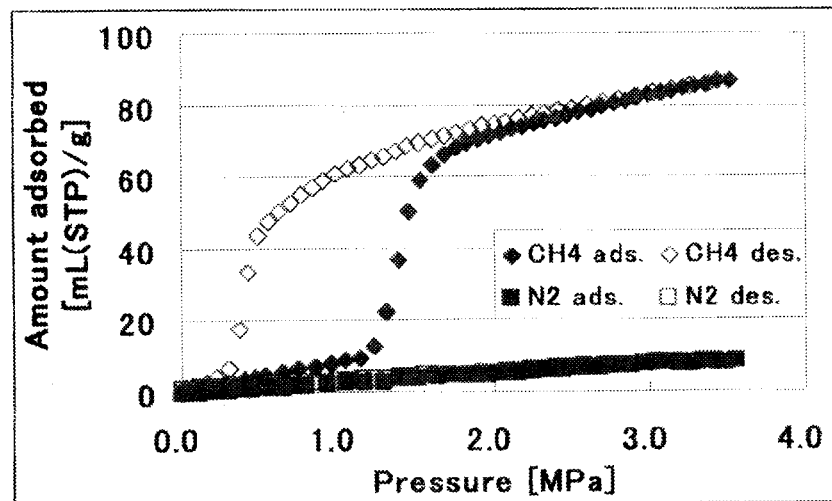
FIG. 25 shows adsorption and desorption isotherms of methane and nitrogen on a metal complex obtained in Synthesis Example 1 at 298 K.

FIG. 25 reveals that since the metal complex obtained in Synthesis Example 1, which satisfies the constituent features of the present invention, selectively adsorbs methane along with the increase in pressure, and releases methane along with the decrease in pressure, the metal complex of the present invention can be used as a material for separating nitrogen and methane.

Example 14

The amounts of ethane and methane adsorbed and desorbed at 273 K on the metal complex obtained in Synthesis Example 1 were measured according to the volumetric method to plot adsorption and desorption isotherms. The results are shown in FIG. 26.

Example 15

The amounts of ethane and methane adsorbed at 298 K by the metal complex obtained in Synthesis Example 1 were measured according to the volumetric method to plot adsorption desorption isotherms. The results are shown in FIG. 27.

Figure 26:
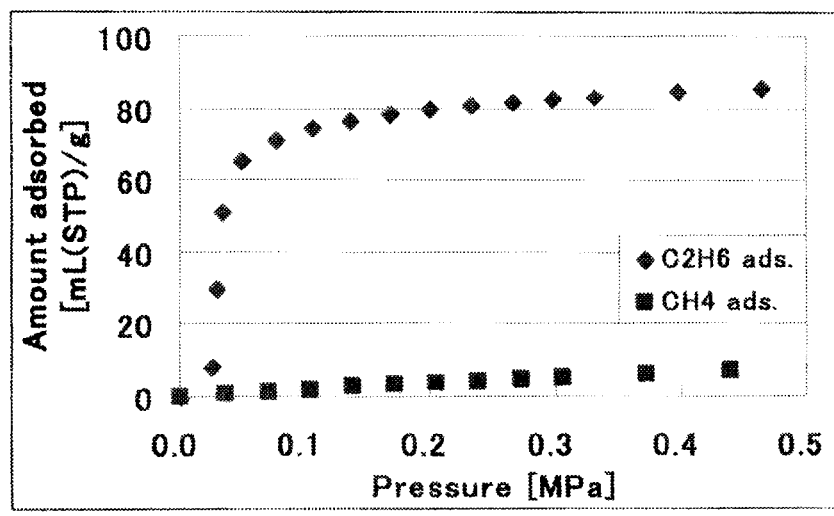
FIG. 26 shows adsorption isotherms of ethane and methane on a metal complex obtained in Synthesis Example 1 at 273 K.
Figure 27:
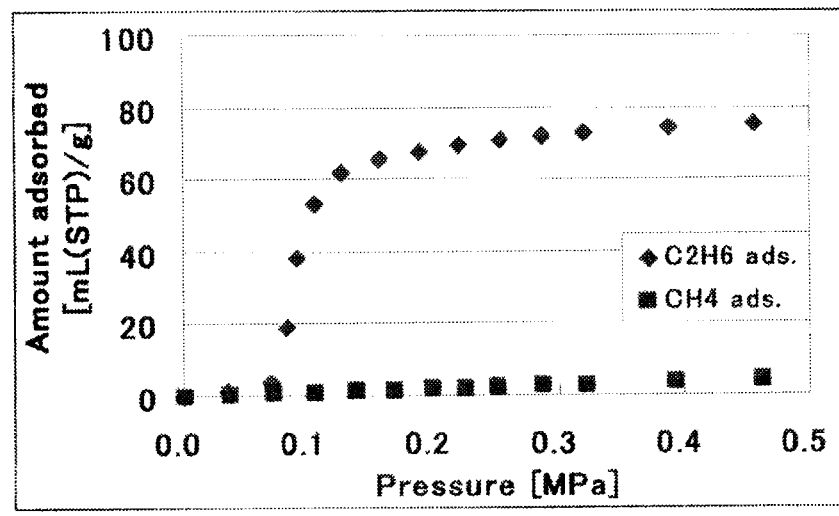
FIG. 27 shows adsorption isotherms of ethane and methane on a metal complex obtained in Synthesis Example 1 at 298 K.

Comparison of FIGS. 26 and 27 reveals that since the adsorption starting pressure of the metal complex obtained in Synthesis Example 1, which satisfies the constituent features of the present invention, depends on the temperature and is controllable, the metal complex of the present invention can be used as a separation material for use in a temperature swing adsorption process.

Example 16

For the metal complex obtained in Synthesis Example 2, the breakthrough curve at 293 K, 0.8 MPa, and at a space velocity of 6 $min^{-1}$ was measured using a gas mixture comprising methane and carbon dioxide in a volume ratio of 60:40, and the gas separation performance was evaluated. The results are shown in FIG. 28.

FIG. 28 indicates that the metal complex obtained in Synthesis Example 2, which satisfies the constituent features of the present invention, preferentially adsorbs carbon dioxide, and enriches methane up to 99.5% or higher. Since the breakthrough time (the period until carbon dioxide is detected in an outlet gas) is long, and only methane can be collected during that period, it is clear that the metal complex of the present invention can be used as a material for separating methane and carbon dioxide. In addition, FIG. 22 reveals that since the metal complex of the present invention releases the adsorbed carbon dioxide with the decrease in pressure, it can be used as a separation material for use in a pressure swing adsorption process.

Example 17

An acrylic elastomer (a methyl methacrylate-butyl acrylate block copolymer: Kurarity™ 2250, produced by Kuraray Co., Ltd.; 2.80 g) was added to 160 mL of chloroform, and dissolved by stirring at 298 K. The metal complex (25.2 g) obtained in Synthesis Example 1 was added to the resulting solution, and the mixture was stirred at 298 K for 5 minutes. After the chloroform was then distilled off under reduced pressure, the resultant was dried for 8 hours at 373 K and 50 Pa to obtain 24.1 g (yield: 86%) of the composition of the acrylic elastomer and the metal complex.

After chloroform (600 mg) was added to the resulting composition (300 mg) of the acrylic elastomer and the metal complex, the mixture was placed in a mill (inner diameter: 3.0 mm; length: 15 mm), subjected to tablet compression at 200 kgf (about 1.96 kN) using a simple tablet press (HAND-TAB-100, produced by Ichihashi Seiki Co., Ltd.), and molded into a pellet shape. The resulting pellet composition was dried at 373 K, 50 Pa for 8 hours, thus obtaining four pellets (270 mg) having a diameter of 3.0 mm and a length of 9.2 mm.

Figure 29:
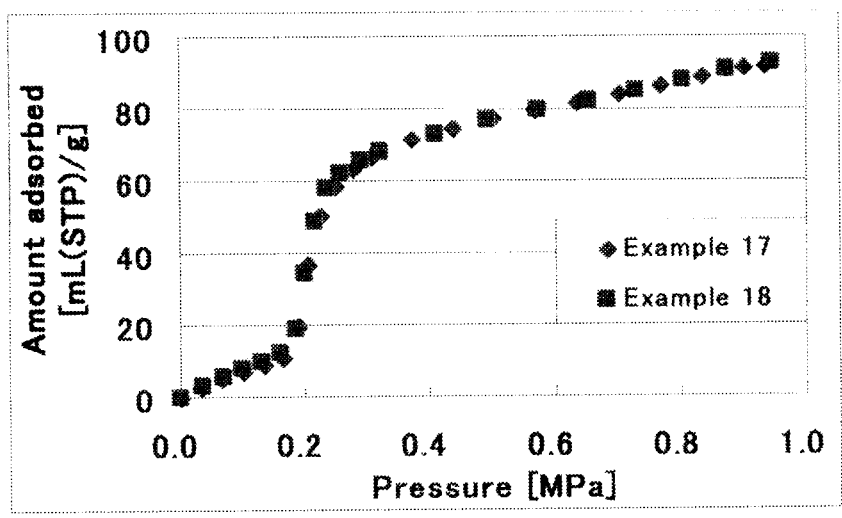
FIG. 29 shows an adsorption isotherm of carbon dioxide on a pellet comprising the metal complex obtained in Synthesis Example 1 at 293 K.

The amount of carbon dioxide adsorbed at 293 K by the obtained metal complex, which had been molded into a pellet shape, was measured according to the volumetric method to plot an adsorption isotherm. The results are shown in FIG. 29 (Example 17).

Example 18

A styrene elastomer (hydrogenated styrene-isoprene block copolymer: Septon™ S2063, produced by Kuraray Co., Ltd.; 2.88 g) was added to 160 mL of chloroform and dissolved by stirring at 298 K. The metal complex (25.9 g) obtained in Synthesis Example 1 was added to the resulting solution, and the mixture was stirred at 298 K for 5 minutes. After the chloroform was then distilled off under reduced pressure, the resultant was dried for 8 hours at 373 K and 50 Pa to obtain 24.5 g (yield: 85%) of the composition of the styrene elastomer and the metal complex.

After chloroform (600 mg) was added to the resulting composition (300 mg) of the styrene elastomer and the metal complex, the mixture was placed in a mill (inner diameter: 3.0 mm; length: 15 mm), subjected to tablet compression at 200 kgf (about 1.96 kN) using a simple tablet press (HAND-TAB-100, produced by Ichihashi Seiki Co., Ltd.), and molded into a pellet shape. The resulting pellet composition was dried at 373 K and 50 Pa for 8 hours to obtain four pellets (260 mg) having a diameter of 3.0 mm and a length of 9.4 mm.

The amount of carbon dioxide adsorbed at 293 K by the obtained metal complex, which had been molded into a pellet shape, was measured according to the volumetric method to plot an adsorption isotherm. The results are shown in FIG. 29 (Example 18).

FIG. 29 reveals that the pellet comprising the metal complex, which satisfies the constituent features of the present invention, adsorbs carbon dioxide along with the increase in pressure. Accordingly, it is clear that the molded product comprising the metal complex of the present invention can be used as an adsorbent material, a storage material, or a separation material for carbon dioxide, etc., and such molded metal complexes can be included in the scope of the right of the present invention.

The invention claimed is:

1. A metal complex, comprising:
    a multivalent carboxylic acid compound,
    at least one metal ion, which is an ion of a metal of Groups 2 to 13 of the periodic table,
    an organic ligand capable of multidentate binding to the metal ion, and
    a $C_1$ or $C_2$ monocarboxylic acid compound, which is a counteranion of a raw material metal salt of the metal ion and is incorporated in the metal complex structure,
    wherein a composition ratio of the multivalent carboxylic acid compound to the monocarboxylic acid compound is from 10:1 to 5,000:1.

2. The metal complex according to claim 1, wherein the multivalent carboxylic acid compound is a dicarboxylic acid compound.

3. The metal complex according to claim 1, wherein the organic ligand capable of multidentate binding is an organic ligand capable of bidentate binding.

4. The metal complex according to claim 3, wherein the organic ligand capable of bidentate binding has a longitudinal length of 7.0 Å or more and 16.0 Å or less.

5. The metal complex according to claim 1, wherein the metal complex is molded into any shape selected from the group consisting of a pellet, a film, a sheet, a plate, a pipe, a tube, a rod, a granule, a special molded product, a fiber, a hollow filament, a woven fabric, a knitted fabric, and a non-woven fabric.

6. An adsorbent material, comprising the metal complex according to claim 1.

7. The adsorbent material according to claim 6, which is a material for adsorbing carbon dioxide, hydrogen, carbon monoxide, oxygen, nitrogen, hydrocarbons comprising from 1 to 4 carbon atoms, noble gases, hydrogen sulfide, ammonia, sulfur oxides, nitrogen oxides, siloxanes, water vapor, or organic vapor.

8. A storage material, comprising the metal complex according to claim 1.

9. The storage material according to claim 8, which is a material for storing carbon dioxide, hydrogen, carbon monoxide, oxygen, nitrogen, hydrocarbons comprising from 1 to 4 carbon atoms, noble gases, hydrogen sulfide, ammonia, water vapor, or organic vapor.

10. A gas storage device, comprising:
    a pressure-resistant container that is hermetically sealed and comprises
        an inlet and outlet for gas,
        a gas storage space inside, and
        the storage material according to claim 8 in the gas storage space.

11. A gaseous-fuel vehicle, comprising an internal combustion engine that obtains driving force from fuel gas supplied from the gas storage device according to claim 10.

12. A separation material, comprising the metal complex according to claim 1.

13. The separation material according to claim 12, which is a material for separating carbon dioxide, hydrogen, carbon monoxide, oxygen, nitrogen, hydrocarbons comprising from 1 to 4 carbon atoms, noble gases, hydrogen sulfide, ammonia, sulfur oxides, nitrogen oxides, siloxanes, water vapor, or organic vapor.

14. The separation material according to claim 12, which is a material for separating methane and carbon dioxide, hydrogen and carbon dioxide, nitrogen and carbon dioxide, ethylene and carbon dioxide, methane and ethane, ethane and ethylene, propane and propene, nitrogen and oxygen, oxygen and argon, nitrogen and methane, or air and methane.

15. A separation method using the separation material according to claim 12, the separation method comprising bringing the metal complex into contact with a gas mixture in a pressure range of 0.01 to 10 MPa.

16. The separation method according to claim 15, which is a pressure swing adsorption process or a temperature swing adsorption process.

\* \* \* \* \*